United States Patent
Lao et al.

(10) Patent No.: US 10,501,784 B2
(45) Date of Patent: *Dec. 10, 2019

(54) SEQUENCE AMPLIFICATION WITH LINEAR PRIMERS

(71) Applicant: LIFE TECHNOLOGIES CORPORATION, Carlsbad, CA (US)

(72) Inventors: Kai Lao, Pleasanton, CA (US); Neil Straus, Emeryville, CA (US); Nanlan Xu, Danville, CA (US)

(73) Assignee: Life Technologies Corporation, Carlsbad, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 15/237,266

(22) Filed: Aug. 15, 2016

(65) Prior Publication Data
US 2017/0107567 A1    Apr. 20, 2017

Related U.S. Application Data

(63) Continuation of application No. 14/101,226, filed on Dec. 9, 2013, now Pat. No. 9,447,463, which is a continuation of application No. 13/333,419, filed on Dec. 21, 2011, now abandoned, which is a continuation of application No. 12/428,196, filed on Apr. 22, 2009, now abandoned.

(60) Provisional application No. 61/125,279, filed on Apr. 23, 2008.

(51) Int. Cl.
| C12Q 1/68 | (2018.01) |
| C12Q 1/6853 | (2018.01) |
| C12Q 1/6844 | (2018.01) |
| C12Q 1/6848 | (2018.01) |

(52) U.S. Cl.
CPC ......... *C12Q 1/6853* (2013.01); *C12Q 1/6844* (2013.01); *C12Q 1/6848* (2013.01); *C12Q 2600/158* (2013.01)

(58) Field of Classification Search
None
See application file for complete search history.

(56) References Cited

U.S. PATENT DOCUMENTS

| 7,176,002 B2 | 2/2007 | Lao et al. |
| 7,575,863 B2 | 8/2009 | Chen et al. |
| 7,642,055 B2 | 1/2010 | Finn et al. |
| 8,323,897 B2 | 12/2012 | Andersen et al. |
| 8,349,563 B2 | 1/2013 | Lao et al. |
| 2004/0209298 A1* | 10/2004 | Kamberov ............. C12N 15/10 435/6.14 |
| 2008/0161197 A1 | 7/2008 | Lao |
| 2009/0291475 A1 | 11/2009 | Lao et al. |
| 2012/0142059 A1 | 6/2012 | Lao et al. |
| 2014/0235845 A1 | 8/2014 | Lao et al. |

OTHER PUBLICATIONS

Dean, F et al., "Comprehensive human genome amplification using multiple displacement amplification", *PNAS*, vol. 99(8), 2002, pp. 5261-5266.
Diatchenko, et al., "Supression substractive hybridization: A method for generating differentially regulated or tissue-specific cDNA probes and libraries", *Proc. Natl. Acad. Sci. USA*, 93:, Jun. 1996, 6025-6030.
Lao, et al., "Whole genome amplification using single-primer PCR", *Biotechnol. J.*, 3: 2008, 378-382.
Mitsuhashi, M, "Technical Report: Part 2. Basic Requirements for Designing Optimal PCR Primers", *Journal of Clinical Laboratory Analysis*, vol. 10, No. 5, 1996, 285-293.
Raghunathan, et al., "Genomic amplification from a single bacterium", *Appl. Environ. Microbiol.*, 71, 2005, 3342-3347.
Siebert, et al., "An improved PCR method for walking in uncloned genomic DNA", *Nucleic Acids Research*, 23(6), 1995, 1087-1088.
Telenius, Hakan et al., "Degenerate Oligonucleotide-Primed PCR: General Amplification of Target DNA by a Single Degenerate Primer", *Genomics*, 13, 1992, 718-725.
Von Eggeling, Ferdinand et al., "Applications of Random PCR" *Cellular and Molecular Biology*, 41(5), 1995, 653-670.
Zhang, et al., "Sequencing genomes from single cells by polymerase cloning", *Nat. Biotechnol.*, 24, 2006, 680-686.
Zhang, et al., "Whole genome amplification from a single cell: Implications for Genetic analysis", *Proc. Natl. Acad. Sci. USA*, 89:, Jul. 1992, 5847-5851.
Zong, Chenghang et al., "Genome-Wide Detection of Single-Nucleotide and Copy-Number Variations of a Single Human Cell", *Science*, 338, 2012, 1622-1626.

* cited by examiner

*Primary Examiner* — Suryaprabha Chunduru

(57) ABSTRACT

The present disclosure relates to the amplification of target nucleic acid sequences for various sequencing and/or identification techniques. The use of these primers, as described herein, allows for the reduction in the amplification of nonspecific hybridization events (such as primer dimerization) while allowing for the amplification of the target nucleic acid sequences.

14 Claims, 18 Drawing Sheets
Specification includes a Sequence Listing.

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<221> NAME/KEY: misc_feature
<222> LOCATION: 31
<223> OTHER INFORMATION: n = a, c, t, or g
<220> FEATURE:
<223> OTHER INFORMATION: Primer

<400> SEQUENCE: 1
tcatgatccg tggagtcggc tttttttttt n                              31

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
tcatgatccg tggagtcggc tttttttttt                                30

<210> SEQ ID NO 3
<211> LENGTH: 40
<212> TYPE: DNA
<213> ORGANISM: Artificial Sequence
<220> FEATURE:
<221> NAME/KEY: misc_feature
<222> LOCATION: (31)...(40)
<223> OTHER INFORMATION: n = a, c, t, or g
<220> FEATURE:
<223> OTHER INFORMATION: Primer

<400> SEQUENCE: 3
tcatgatccg tggagtcggc tttttttttt nnnnnnnnnn                     40

<210> SEQ ID NO 4
<211> LENGTH: 48
<212> TYPE: DNA
<213> ORGANISM: Artificial Sequence
<220> FEATURE:
<221> NAME/KEY: misc_feature
<222> LOCATION: (38)...(48)
<223> OTHER INFORMATION: n = a, c, t, or g
<220> FEATURE:
<223> OTHER INFORMATION: Primer

<400> SEQUENCE: 4
tcatgatccg tggagtcggc tttttttttt gatcatgann nnnnnnnn            48
```

SEQUENCE AMPLIFICATION WITH LINEAR PRIMERS

RELATED APPLICATIONS

This application is a Continuation application of U.S. patent application Ser. No. 14/101,226, filed Dec. 9, 2013, now U.S. Pat. No. 9,447,463, issued Sep. 20, 2016; which is a Continuation application of U.S. patent application Ser. No. 13/333,419, filed Dec. 21, 2011, now abandoned; which is a Continuation application of U.S. patent application Ser. No. 12/428,196, filed Apr. 22, 2009, now abandoned; which claims a priority benefit under 35 U.S.C. § 119(e) from U.S. Provisional Application No. 61/125,279, filed Apr. 23, 2008, all of which are incorporated herein by reference in their entireties.

SEQUENCE LISTING

The present application is being filed along with a Sequence Listing in electronic format. The Sequence Listing is provided as a file entitled SEQ_LIST_ABIOS-96A.txt, created Apr. 17, 2009, last modified Apr. 21, 2009, which is 1,188 bytes in size. The information in the electronic format of the Sequence Listing is incorporated herein by reference in its entirety.

FIELD

The invention relates to methods and compositions for amplifying nucleic acid sequences.

INTRODUCTION

Whole genome amplification (WGA) can be a valuable technique for amplification of a genome from minimal or limiting amounts of DNA for subsequent molecular genetic analysis.

Whole genome amplification can be performed using either conventional or nonconventional PCR amplification methods. Conventional PCR entails the amplification and subsequent detection of specific DNA sequences which are precisely characterized in length and sequence using non-degenerate primers, while random, "non-conventional" PCR involves universal amplification of prevailing DNA or amplification of unknown intervening sequences which are not generally defined in length or sequence using degenerate primers.

SUMMARY

Some of the present embodiments allow target nucleic acid sequences to be amplified using at least one linear primer. In some embodiments, the linear primer includes a random or degenerate region. In some embodiments, the linear primer includes a noncomplementary region to reduce the likelihood of nonspecific hybridization of the primer (such as primer dimers) during subsequent amplification steps. In some embodiments the linear primer includes a universal priming region. In some embodiments, no more than one linear primer is used.

In some embodiments, the linear primer includes a universal priming region positioned after and distinct from the random region and optionally a noncomplementary region. The noncomplementary region and/or the universal priming region can be configured so that a sequence associated with a target sequence that has been amplified by the linear primer (a double-extended linear primer) forms a self-hybridized structure involving the noncomplementary region and/or the universal priming region hybridized to complementary sequences of the noncomplementary region and/or the universal priming region. This self-hybridized structure can allow for the selective amplification of longer sections of target nucleic acid sequence over shorter sections. The presence of the noncomplementary region can assist in reducing nonspecific binding of various primers throughout the amplification process. The linear primer can include sequences and structures in addition to those listed above.

In some embodiments, a method of amplifying a nucleic acid sequence in a parallel sequencing technique is provided. The method can comprise, consist, or consist essentially of hybridizing a 3' target specific region of a first linear primer to a first part of a target nucleic acid sequence, wherein the first linear primer comprises a universal priming region that is distinct from the 3' target specific region, and wherein the 3' target specific region is a random region that is less than 6 nucleotides in length. The method can further comprise extending the first linear primer that is hybridized to the target nucleic acid sequence to form an extended linear primer and hybridizing a second linear primer to a complementary part of the target nucleic acid sequence of the extended linear primer, wherein the second linear primer comprises a same universal priming region as the first linear primer. The method can further comprise extending the second linear primer to form a double-extended linear primer and amplifying the double-extended linear primer using an amplification primer, wherein the amplification primer comprises a sequence that is the same as a sequence of the universal priming region, and wherein a double-extended linear primer comprising a first insert section is selectively amplified over a double-extended linear primer comprising a second insert section. The method can further comprise adding a third primer that comprises a sequence that is complementary to a sequence within first insert section and performing an amplification reaction using the third primer to amplify the target nucleic acid sequence within the first insert section of the double-extended linear primer, wherein the double-extended linear primer comprising the first insert has its insert section selectively amplified compared to the double-extended linear primer comprising the second insert, wherein the first insert section is larger than the second insert section. The method can further comprise performing a parallel sequencing reaction on an amplified product from the amplification reaction using a third and further fourth primers. In some embodiments, the double-extended linear primer comprising the first insert section is selectively amplified over the double-extended linear primer comprising a second insert section when the double extended linear primer itself is amplified.

In some embodiments, a method of amplifying a nucleic acid sequence in a parallel sequencing technique is provided. The method can comprise, consist, or consist essentially of hybridizing a 3' target specific region of a first linear primer to a first part of a target nucleic acid sequence, wherein the first linear primer comprises a universal priming region that is distinct from the 3' target specific region, wherein the 3' target specific region is a random region, and wherein the first linear primer and the target nucleic acid sequence are within a volume of liquid that is more than 60 nl. The method can further comprise extending the first linear primer that is hybridized to the target nucleic acid sequence to form an extended linear primer and hybridizing a second linear primer to a complementary part of the target nucleic acid sequence of the extended linear primer, wherein the second linear primer comprises a same universal priming region as the first linear primer. The method can further comprise extending the second linear primer to form a double-extended linear primer and amplifying the double-extended linear primer using an amplification primer, wherein the amplification primer comprises a sequence that is the same as a sequence of the universal priming region, and wherein a double-extended linear primer comprising a first insert section is selectively amplified over a double-extended linear primer comprising a second insert section. The method can further comprise adding a third primer that comprises a sequence that is complementary to a sequence within the first insert section and performing an amplification reaction using the third and fourth primers to amplify the target nucleic acid sequence within the first insert section of the double-extended linear primer, wherein the double-extended linear primer comprising the first insert has its insert section selectively amplified compared to the double-extended linear primer comprising the second insert section, and wherein the first insert section is larger than the second insert section. The method can further comprise performing a parallel sequencing reaction on an amplified product from the amplification reaction using the third primer.

In some embodiments, a method of amplifying a nucleic acid sequence in a parallel sequencing technique is provided. The method can comprise, consist, or consist essentially of hybridizing a 3' target specific region of a first linear primer to a first part of a target nucleic acid sequence, wherein the first linear primer comprises a universal priming region that is separate from the 3' target specific region, wherein the 3' target specific region is a random region, and wherein the random region comprises at least one nucleotide that is not an adenine or a guanine. The method can further comprise extending the first linear primer that is hybridized to the target nucleic acid sequence to form an extended linear primer and hybridizing a second linear primer to a complementary part of the target nucleic acid sequence of the extended linear primer, wherein the second linear primer comprises a same universal priming region as the first linear primer. The method can further comprise extending the second linear primer to form a double-extended linear primer and amplifying the double-extended linear primer using an amplification primer, wherein the amplification primer comprises a sequence that is the same as a sequence of the universal priming region, wherein a double-extended linear primer comprising a first insert section is selectively amplified over a double-extended linear primer comprising a second insert section because the double-extended linear primer comprising a second insertion section forms a self-hybridized structure. The method can further comprise adding a third primer that comprises a sequence that is complementary to a sequence within the first insert section and adding a fourth primer that comprises a sequence that is complementary to a sequence within the first insert section. The method can further comprise performing an amplification reaction using the third and fourth primers to amplify the target nucleic acid sequence within the first insert section of the double-extended linear primer, wherein the double-extended linear primer comprising the first insert has its insert section selectively amplified compared to the double-extended linear primer comprising the second insert, wherein the first insert section is larger than the second insert section. The method can further comprise performing a parallel sequencing reaction on an amplified product from the amplification reaction using the third and fourth primers.

In some embodiments, kits and/or components for the above methods are provided. In some embodiments, the kit includes one or more linear primers (which can be degenerate) and materials for parallel sequencing, such as for supported oligo ligation detection sequencing. The kits can also include the relevant amplification primer and insert primers.

In some embodiments, a single primer (which can optionally include a degenerate 3' target specific region) is used to initially prime to a target sequence.

In some embodiments, the method comprises selectively amplifying a nucleic acid sequence comprising the processes of hybridizing a 3' target specific region of a first primer to a first part of a target nucleic acid sequence, wherein the first primer comprises a universal priming region that is distinct from the 3' target specific region, and wherein the 3' target specific region is a random region; extending the first primer that is hybridized to the target nucleic acid sequence to form an extended primer; hybridizing a second primer to a complementary part of the target nucleic acid sequence of the extended primer, wherein the second primer comprises a same universal priming region as the first primer; extending the second primer to form a double-extended primer; amplifying the double-extended primer using an amplification primer, wherein the amplification primer comprises a sequence that is the same as a sequence of the universal priming region, wherein a double-extended primer comprising a first insert section that is at least 100 nucleotides in length is selectively amplified over a double-extended primer comprising a second insert section that is less than 100 nucleotides in length; adding a third primer that comprises a sequence that is complementary to a sequence within the first insert section; adding a fourth primer that comprises a sequence that is complementary to a sequence within the first insert section; and performing an amplification reaction using the third primer and fourth primer to amplify the target nucleic acid sequence within the first insert section of the double-extended primer, wherein the double-extended primer comprising the first insert has its insert section selectively amplified compared to the double-extended primer comprising the second insert section.

DETAILED DESCRIPTION OF VARIOUS EMBODIMENTS

Figure 1A:
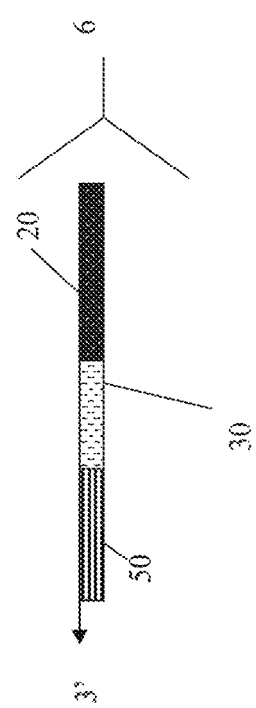
FIG. 1A depicts one embodiment of a linear primer.

The use of linear primers in the amplification of a target nucleic acid sequence is described herein. One problem that can occur in target nucleic acid amplification is inadvertent primer dimerization. This can be of concern when random priming regions, degenerate priming regions, universal priming regions, or some combination thereof are used. As disclosed herein, linear primers can be used to produce complementary sequences on either end of a target sequence to be amplified. This resulting product (a double-extended linear primer) can self-hybridize via the complementary sequences. Products that include insert sections that are very short will self-terminate from subsequent amplification, as they will rapidly self-hybridize. Products that include an insert section that is relatively long can remain viable templates for continued amplification. Thus, primer dimers and other short products are selectively removed from the amplification process.

In some embodiments, the above general approach can be applied to genomic analysis with especially advantageous results. For example, presently, there are two basic methods for amplification, isothermal multiple displacement amplification ("MDA") and thermal cycled methods, such as primer extension preamplification (PEP) or degenerate oligonucleotide primed PCR (DOP-PCR). One problem with such techniques is that for very low amounts of input DNA the large amount of priming between the vast excess of random primers produces excessive amounts of background random sequence. This background random sequence can be disastrous for sequencing of unknown genomes. To get around this using the MDA amplification method, constrained random primers of randomized A, G sequence have been used, where they exclude thymine and/or cytosine. Even the addition of one such base (e.g., T), to the constrained random priming significantly degrades the resulting product. Another approach using MDA is to constrain the reaction to very small volumes, 60 nl or less, using microfluidic devices.

Some of the presently disclosed embodiments address some or all of the above problems without some or all of the previous constraints. Thus, in some embodiments, random or degenerate priming regions can include nucleotides other than A and/or G. Furthermore, in some embodiments, larger volumes (e.g., above 60 nl) can be used during amplification. In addition, in some embodiments, especially short 3' target specific regions (e.g., less than 7 nucleotides in length) can be used for the initial priming events. As will be appreciated by one of skill in the art, various embodiments herein can have one or more of the above properties, and one or more of the above properties can be useful and overcome various obstacles.

The above and additional embodiments are described in greater detail below. Following the definition and alternative embodiments section provided immediately below, a general description of linear primers and their use is provided, followed by a description of specific embodiments involving linear primers in especially advantageous and superior embodiments. Following these sections, a brief description providing additional embodiments is provided along with a series of specific examples.

Some Definitions and Alternative Embodiments

As used herein, the term "target nucleic acid sequence" refers to a polynucleotide sequence that is sought to be detected, sequenced, and/or characterized in a sample. The target nucleic acid sequence can be obtained from any source and can include any number of different compositional components. For example, the target can be nucleic acid (e.g. DNA or RNA), transfer RNA, mRNA, siRNA, and can include nucleic acid analogs or other nucleic acid mimic. The target can be methylated, non-methylated, or both. The target can be bisulfite-treated and non-methylated cytosines converted to uracil. Further, it will be appreciated that "target nucleic acid sequence" can refer to the target nucleic acid sequence itself, as well as surrogates thereof, for example amplification products, and native sequences. In some embodiments, the target nucleic acid sequence is a miRNA molecule. In some embodiments, the target nucleic acid sequence lacks a poly-A tail. In some embodiments, the target nucleic acid sequence is a short DNA molecule derived from a degraded source, such as can be found in, for example but not limited to, forensics samples (see for example Butler, 2001, Forensic DNA Typing: Biology and Technology Behind STR Markers). In some embodiments, the target nucleic acid sequences of the present teachings can be present or derived from any of a number of sources, including without limitation, viruses, prokaryotes, eukaryotes, for example but not limited to plants, fungi, and animals. These sources can include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil samples), research samples generally, purified samples generally, cultured cells, and lysed cells.

It will be appreciated that target nucleic acid sequences can be isolated or obtained from samples using any of a variety of procedures known in the art, for example the Applied Biosystems ABI Prism™ 6100 Nucleic Acid Prep-Station, and the ABI Prism™ 6700 Automated Nucleic Acid Workstation, Boom et al., U.S. Pat. No. 5,234,809, mirVana RNA isolation kit (Ambion), etc. It will be appreciated that target nucleic acid sequences can be cut or sheared prior to analysis, including the use of such procedures as mechanical force, sonication, heat, restriction endonuclease cleavage, or any method known in the art. Cleaving can be done specifically or non-specifically. In general, the target nucleic acid sequences of the present teachings will be single stranded, though in some embodiments the target nucleic acid sequence can be double stranded, and a single strand can be produced by denaturation. In some embodiments, the target nucleic acid sequence is genomic DNA.

As will be appreciated by one of skill in the art, the term "target nucleic acid sequence" can have different meanings at different steps throughout the method. For example, in an initial sample, there can be a target nucleic acid sequence that is 2 kb in length. When this is amplified by the linear primer to form a double-extended linear primer, part of the target nucleic acid sequence can be contained within the double-extended linear primer; however, not all of the target nucleic acid sequence need be contained within the double-extended linear primer. Regardless of this, the section of the target nucleic acid sequence that is amplified can still be referred to as the "target nucleic acid sequence" (in part because it will still indicate the presence or absence of the large target nucleic acid sequence of which it is a part). Similarly, when the section of the insert section, which contains the target nucleic acid sequence, is amplified by the insert amplification primers it can also be described as amplifying the "target nucleic acid sequence." One of skill in the art will appreciate that, likely, the length of the target nucleic acid sequence will decrease as the sequence is processed further. When desired, each target nucleic acid sequence in each step can be specifically designated as an "initial target nucleic acid sequence," a "double-extended linear primer target nucleic acid sequence", and an "insert section target nucleic acid sequence." Additionally, one of skill in the art will appreciate that the sequence that one is interested in determining if present in a sample can be a separate sequence from a target nucleic acid sequence that is amplified. For example, the sequences can be in linkage disequilibrium or from a different part of a gene or stretch of nucleic acids. Such sequences can be termed "inquiry target nucleic acid sequences."

The term "whole genome amplification" does not require that 100% of a genome be amplified. Rather, partial amounts of the genome can be amplified and still qualify as a whole genome amplification process. Thus, the above term simply denotes that amplification across a genome has occurred, and can be characterized as a genome wide amplification. The amplification process is one that amplifies a significant portion of the genomic nucleic acid in a sample. In some embodiments, the significant portion is at least 30%, for example, 30, 30-40, 40-50, 50-60, 60-70, 70-80, 80-90, 90-95, 95-98, 98-99, 99-100% of the genomic nucleic acid in a sample. As will be appreciated by one of skill in the art, the genomic nucleic acid need not be directly derived from a biological host and can itself be the result of some previous manipulation or amplification.

As used herein, the term "linear primer" refers to a molecule comprising a 3' target specific portion and a universal priming region. It will be appreciated that the linear primers can be comprised of ribonucleotides, deoxynucleotides, modified ribonucleotides, modified deoxyribonucleotides, modified phosphate-sugar-backbone oligonucleotides, nucleotide analogs, or combinations thereof. For some illustrative teachings of various nucleotide analogs etc, see Fasman, 1989, Practical Handbook of Biochemistry and Molecular Biology, pp. 385-394, CRC Press, Boca Raton, Fla., Loakes, N. A. R. 2001, vol 29:2437-2447, and Pellestor et al., Int J Mol Med. 2004 April; 13(4):521-5), references cited therein, and recent articles citing these reviews. It will be appreciated that the selection of the linear primers to query a given target nucleic acid sequence, and the selection of which collection of target nucleic acid sequence to query in a given reaction with which collection of linear primers, will involve procedures generally known in the art, and can involve the use of algorithms to select for those sequences with desirable features, such as, minimal secondary and tertiary structure, those targets with minimal sequence redundancy with other regions of the genome, those target regions with desirable thermodynamic characteristics, and other parameters desirable for the context at hand. In some embodiments, a universal primer is included within the linear primer. In some embodiments, a non-complementary region or sequence is included within the linear primer. In some embodiments, an identifying portion is included within the linear primer.

In some embodiments, the primer is not a "linear" primer. For example, in some embodiments, the primer can be looped. The term "target primer" or simply "primer" can be used to generically refer to both looped and linear primers. As will be appreciated by those of skill in the art, the present disclosure, while focused on "linear primers" teaches embodiments and aspects that are also applicable to "loopable primers." Thus, unless explicitly stated, the present teachings and disclosures are applicable to linear primer and loopable primers.

As used herein, the term "3' target-specific portion" refers to a single stranded portion of a linear primer that is complementary to at least a portion of a target nucleic acid sequence. The 3' target-specific portion is located downstream from the universal priming region and/or noncomplementary region of the linear primer. Generally, the 3' target-specific portion is between 4 and 15 nucleotides long and can be between 6 and 12 nucleotides in length. In some embodiments, the 3' target-specific portion is 7 nucleotides long. It will be appreciated that, in light of the present disclosure, routine experimentation can be used to optimize length, and that 3' target-specific portions that are longer than 8 nucleotides or shorter than 6 nucleotides are also contemplated by the present teachings. In some embodiments, modified bases such as LNA can be used in the 3' target specific portion to increase the stability, for example by increasing the Tm of the linear primer (see for example Petersen et al., Trends in Biochemistry (2003), 21:2:74-81). In some embodiments, universal bases can be used in the 3' target specific portion, for example to allow for smaller libraries of linear primers. Universal bases can also be used in the 3' target specific portion to allow for the detection of unknown targets (e.g., targets for which specific binding sequences are not known). For some descriptions of universal bases, see for example Loakes et al., Nucleic Acids Research, 2001, Volume 29, No. 12, 2437-2447. In some embodiments, modifications including but not limited to LNAs and universal bases can improve reverse transcription specificity and potentially enhance detection specificity. In some embodiments, the 3' target-specific region does not consist of all adenines. In some embodiments, the 3' target-specific region does not consist of all thymines.

In some embodiments, the 3' target-specific region includes or is a degenerate region, a random region, a specific region, or a known sequence. In some embodiments, the 3' target specific region includes a combination of these regions. In some embodiments, the 3' target specific regions have a Tm of between about 5° C. and 50° C. In some embodiments, a 15-mer has a Tm of less than about 60° C.

The term "degenerate primer" when used herein refers to a mixture of similar primers with differing bases at the varying positions (Mitsuhashi M, J Clin Lab Anal, 10(5):285 93 (1996); von Eggeling et al., Cell Mol Biol, 41(5):653 70 (1995); (Zhang et al., Proc. Natl. Acad. Sci. USA, 89:5847 5851 (1992); Telenius et al., Genomics, 13(3):718 25 (1992)). Such primers can include inosine as inosine is able to base pair with adenosine, cytosine, guanine or thymidine. Degenerate primers allow annealing to and amplification of a variety of target sequences that can be related. Degenerate primers that anneal to target DNA can function as a priming site for further amplification. A degenerate region is a region of a primer that varies, while the rest of the primer can remain the same. Degenerate primers (or regions) denote more than one primer and can be random. A random primer (or regions) denotes that the sequence is not selected, and it can be degenerate but does not have to be. In some embodiments, the 3' target specific regions have a Tm of between about 5° C. and 50° C. In some embodiments, a 15-mer has a Tm of less than about 60° C.

A "specific region" (in contrast to a "3' target specific region" which is a broader genus) is able to bind to a genomic sequence occurring in a genome with a frequency. In some embodiments, this frequency is between about 0.01% and 2.0%, such as, for example, between about 0.05% and 0.1% or between about 0.1% and 0.5%. In some embodiments, the length of the "specific region" of a primer depends mainly on the averaged lengths of the predicted PCR products based on bioinformatic calculations. The definition includes, without limitation, a "specific region" of between about 4 and 12 bases in length. In more particular embodiments, the length of the 3' specific region can, for example, be between about 4 and 20 bases, or between about 8 and 15 bases. Specific regions having a Tm of between about 10° C. and 60° C. are included within the definition. The term, "specific primer," when used herein refers to a primer of specified sequence. An example of a specific region would be a region for priming for the amplification of a STR locus The term "random region" as used herein refers to a region of an oligonucleotide primer that is able to anneal to unspecified sites in a group of target sequences, such as in a genome. The "random region" facilitates binding of the primer to target DNA and binding of the polymerase enzyme used in PCR amplification to the duplex formed between the primer and target DNA. The random region nucleotides can be degenerate or non-specific, promiscuous nucleobases or nucleobase analogs. The length of the "random region" of the oligonucleotide primer, among other things, depends on the length of the specific region. In certain embodiments, without limitation, the "random region" is between about 2 and 15 bases in length, between about 4 and 12 bases in length or between about 4 and 6 bases in length. In another embodiment, the specific and random regions combined will be about 9 bases in length, e.g., if the specific region has 4 bases, the random region will have 5 bases.

In some embodiments, the 3' target-specific portion comprises both a specific region and a random region or degenerate region. In other embodiments, the 3' target-specific portion includes a specific region, a random region or a degenerate region.

In some embodiments, the 3' target-specific portion comprises both a specific region and a random region or degenerate region. In other embodiments, the 3' target-specific portion includes a specific region, and a random region or a degenerate region. In other embodiments, the 3' target specific region of the linear primer only includes a specific region, a random region, or a degenerate region.

In some embodiments, the term "universal region," "universal primer region," "universal priming region" as used herein refers to a region of an oligonucleotide primer that is designed to have no significant homology to any segment in the genome. However, given that a noncomplementary region can be included in the linear primer, nonspecific priming can be further reduced; thus, this is not necessarily required for all embodiments. In its broadest use, the terms denote a region that allows for priming with a known primer. In some embodiments, this primer is common to at least one other nucleic acid sequences. In some embodiments, the "universal priming region" meets all the requirements for a normal oligonucleotide primer, such as lack of secondary structure, an appropriate Tm, and an appropriate GC content and can be between about 12 and 35 bases in length, between about 15 and 25 bases in length or between about 18 and 22 bases in length. However, as will be appreciated by one of skill in the art, the universal priming region, when part of the linear primer, will be part of a larger structure. Additionally, because the universal priming region will be part of a larger primer, the universal priming region need only function as part of the entire linear primer. As such, in these embodiments, the universal priming region need only assist in priming, as described in detail below. In other embodiments, the universal priming region functions independently as a priming site. In some embodiments, the universal priming region is the same as the noncomplementary region or they share some of the same nucleic acid sequences. "Universal priming site" when used herein refers to a "universal priming region" of a primer that can function as a site to which universal primers anneal for priming of further cycles of DNA amplification. In some embodiments, the linear primer includes a universal priming region. The term "universal primer" as used herein refers to a primer that consists essentially of a "universal region".

As used herein, the "noncomplementary region" refers to a nucleic acid sequence in a linear primer or product thereof. In some embodiments, the noncomplementary region is a sequence that is present in at least some of the various primers or sequences in a reaction mixture. In some embodiments, the sequence is common in all or less than all of the primers used, for example 100, 100-99, 99-95, 95-90, 90-80, 80-70, 70-60, 60-50, 50-40, 40-30, 30-20, 20-10, 10-5, 5-1, 1% or less. Thus, in some embodiments, the primers for the target amplification all contain the same noncomplementary sequence. In some embodiments, the primers in subsequent steps (or a percent as noted above) also have the same noncomplementary region. As will be appreciated by one of skill in the art, the presence of similar sequences across various primers will reduce the likelihood that primer dimerization will occur (as the primers will be less likely to hybridize to one another). In some embodiments, the noncomplementary region is noncomplementary with respect to sequences in the target nucleic acid sequence. This embodiment is described in more detail below. In some embodiments, the noncomplementary region is both present in various primers (thereby reducing primer dimerization) and noncomplementary to sequences in the target sequences (e.g., a relatively long series of thymines)

The presence of the noncomplementary sequence need not absolutely prevent the occurrence of primer dimerization or other forms of nonspecific hybridization in every situation. In some embodiments, the presence of the noncomplementary region reduces the likelihood of these undesired forms of hybridization from occurring. In some embodiments, any decrease is sufficient, for example, less than 100% of the dimers that would have occurred without the noncomplementary region, e.g., 100-99, 99-98, 98-95, 95-90, 90-80, 80-70, 70-60, 60-50, 50-40, 40-30, 30-20, 20-10, 10-5, 5-1, or less of the original primer dimers will occur when the noncomplementary region is present in the linear primer. In some embodiments, the presence of the noncomplementary region decreases likelihood of nonspecific amplification or amplification of undesirably small sections of target nucleic acid sequence. Additionally, while the noncomplementary sequence can be the same in all of the primers or linear primers used, it need not be the same. For example, in some embodiments, the noncomplementary regions, while not hybridizing, are not the same sequences (e.g., TTTT vs. CCCC) in different primers. In other embodiments, the noncomplementary regions are similar, but not identical, (e.g., TTTT vs. TTTC). In other embodiments, the noncomplementary regions are completely different types or sequences of nucleic acids; however, they will still reduce the likelihood of various forms of nonspecific hybridization. As will be appreciated by one of skill in the art, the length of the noncomplementary region can vary and the length required can depend on the various reaction conditions and the sequences present in the target sample, issues that can readily be determined by one of skill in the art.

In some embodiments, the noncomplementary region is effective at reducing the nonspecific hybridization of an amplification primer. The amplification primer can have a region that hybridizes to the noncomplementary region (as well as a region that can hybridize to the universal priming region). Thus, the amplification primer can be more specific for the double-extended linear primer products rather than other nonspecific priming events that could occur if the amplification primer only contained a universal priming region. Thus, in some embodiments, the presence of a noncomplementary region in the linear primer can assist in reducing subsequent nonspecific amplification.

In some embodiments, the noncomplementary region is at least 7-15 nucleotides in length. In some embodiments, the noncomplementary region comprises a series of thymine nucleotides. In some embodiments, the noncomplementary region is 8-12 thymines. In some embodiments, the noncomplementary region only includes 5, 6, 7, 8, 9, 10, 11, 12, 13, 14, 15, 16, 17, 18, 19, or 20 thymines (T), adenines (A), or similar nucleotides (such as artificial nucleotides). In some embodiments, the noncomplementary region is a series of thymines (0-10 nucleotides). In some embodiments, there is no noncomplementary region present in the primer or methods.

As will be appreciated by one of skill in the art, while the term "noncomplementary" can denote that the sequence does not significantly or functionally complement another sequence in a mixture, there will be sequences that can hybridize to the noncomplementary region. For example, in a double-extended linear primer (FIG. 3) there is both the linear primer and the linear primer complement. Additionally, as noted above, in some embodiments, the amplification primer can also include a sequence that can hybridize to the noncomplementary region.

The term "does not effectively hybridize" denotes that the amount of hybridization that occurs is such that a significant reduction in primer dimerization or other forms of nonspecific hybridization occurs.

As used herein, the "target binding site" refers to a nucleic acid sequence, in the target nucleic acid sequence, where the 3' target-specific portion of the linear primer can or is configured to hybridize to. As will be appreciated by one of skill in the art, this section can be part of the target nucleic acid sequence and can therefore be gDNA or other nucleic acid sequences.

As used herein, the "extended linear primer" refers to a nucleic acid sequence that has been extended from a linear primer hybridized to a target binding site. The extended linear primer can include the linear primer, along with a sequence that is effectively complementary to a sequence that is contained within the target sequence (in addition to the target binding sequence). In some embodiments, the extended portion of the extended linear primer (that is to become the longer double-extended linear primer) is at least 100 nucleotides in length. In some embodiments, this extended portion is at least 200 nucleotides in length. In some embodiments, this extended portion is not more than 10 kb in length. As will be appreciated by one of skill in the art, those double-extended linear primers that are to become the shorter double extended linear primer can be shorter than the above ranges. In addition, in some embodiments, other lengths are contemplated. As will be appreciated by one of skill in the art, the "extended linear primer" will include a linear primer; however, it will not need to serve as a primer itself.

As used herein, the "linear primer complement" refers to a nucleic acid sequence that is the complement of the linear primer. As will be appreciated by one of skill in the art, the sequence of the linear primer complement can still form a linear primer itself. Additionally, any noncomplementary region in the linear primer complement will be complementary to the relevant section in the linear primer. An example of a linear primer complement can be found in FIG. 3, on the right hand side of sequence 4, including sections 20' and 30'. One of skill in the art will appreciate that section 52 can also be present.

As used herein, the "universal region complement" refers to a nucleic acid sequence that is the complement of the universal region.

The term "double-extended linear primer" refers to a nucleic acid sequence that has been formed by extending a linear primer that is hybridized to an extended linear primer. In other words, the nucleic acid sequence has been extended twice via linear primers. In some embodiments, the term "double extended linear primer" simply means that there is a nucleic acid sequence that includes a linear primer, a target sequence, and a linear primer complement; the method by which it is made is not relevant. In some embodiments, the term "double extended linear primer" simply means that there is a nucleic acid sequence that includes at least a universal region, a target sequence, and a universal region complement; the method by which it is made is not relevant. As will be appreciated by one of skill in the art, the "double-extended linear primer" can include a linear primer and a linear primer complement; however, it does not necessarily need to serve as a primer itself.

Figure 3:
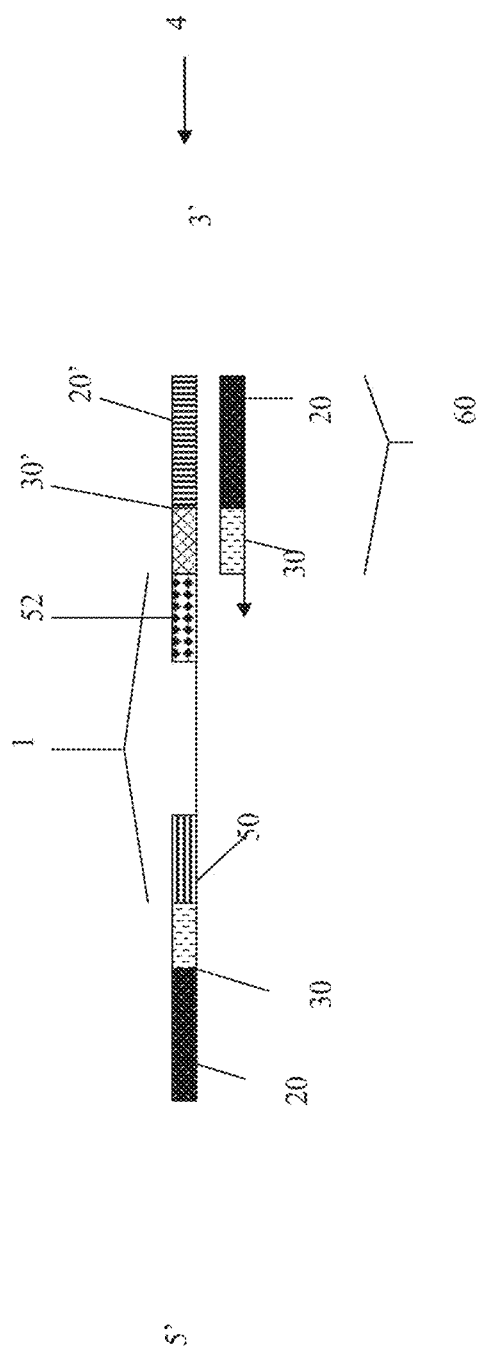
FIG. 3 depicts an embodiment of using a linear primer.

The "amplification primer" can be used for amplifying the double extended linear primer. An example of such a primer is depicted in FIG. 3, as 60. In some embodiments, the amplification primer comprises, consists, or consists essentially of the universal priming region 20. In some embodiments, the primer comprises, consists, or consists essentially of the universal priming region 20, a 3' target specific region 50 and/or a noncomplementary region 30. In some embodiments, the amplification primer is a second linear primer. In some embodiments, the amplification primer is not complementary to a first linear primer. In some embodiments, the amplification primer has at least some of the same sequence as the linear primer. In some embodiments, the amplification primer includes a sequence that is the same as the noncomplementary region. In some embodiments, the amplification primer includes a sequence that is the same as the universal priming region. As will be appreciated by one of skill in the art, the sequences need not be identical in all embodiments, as sequences that still selectively hybridize to the desired location can be employed as well. In some embodiments, the amplification primer is between 10-40 nucleotides long, such as a 30-mer. In some embodiments the amplification primer is 14 nucleotides long. In some embodiments, the amplification primer includes a "universal reverse primer," which indicates that the sequence of the reverse primer can be used in a plurality of different reactions querying different target nucleic acid sequences, but that the amplification primer nonetheless can be the same sequence. In some embodiments, the amplification primer includes a tail region that is not complementary to the sequence that the rest of the primer hybridizes to.

Figure 4:
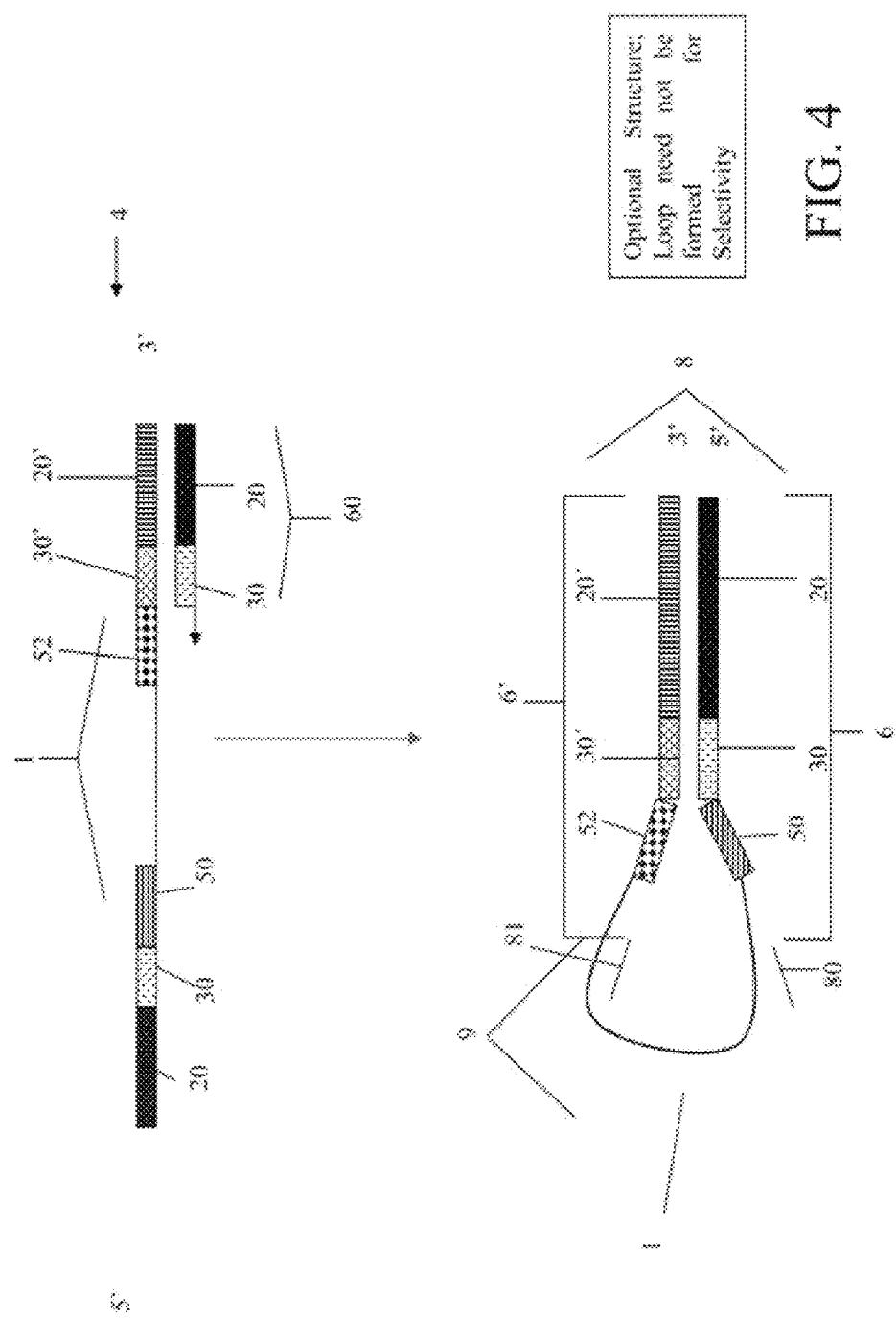
FIG. 4 depicts an embodiment of using a linear primer.

The term "insert section" "capture section", or "target section" refers to the section between the linear primer and the linear primer complement (including the sequence that is bound by the linear primer). In other words, the "insert section" or "insert target" or "capture section", or "target section" refers to the section from one 3' target specific region to a second 3' target specific region, as shown in FIG. 4. In some embodiments, the insert section includes the 3' target specific region as well; thus, the insert section includes 52 and 50 in FIG. 4. As will be appreciated by one of skill in the art, in some embodiments, the insert section 9 can be looped, such as by the hybridization of the linear primer and the linear primer complement in a double-extended primer 8, as shown in FIG. 4, (e.g., the loop formed by the self-hybridization of the double-extended linear primer). However, in other embodiments, the insert section or target section are not actually looped during various amplification steps (although they will be looped for the shorter insert sections, such as primer dimers, that are not to be amplified). As described in more detail below, even when not part of a looped structure, the length of the insert section or target section can still influence the amplification of the section. For example, shorter length insert sections will result in closer to zero order reaction kinetics between the universal region and its complement, while longer insert sections will increase the distance between the universal region primer and its complement, resulting in slower reaction kinetics. Thus, double extended linear primers need not be looped in order to allow for selective amplification of longer insert sections over shorter insert sections. As will be appreciated by one of skill in the art, the linear primer and the linear primer complement will include random regions, which will be complementary to the initial target nucleic acid sequence. Thus, one can characterize the linear primer and its complement as including part of the insert section or the target nucleic acid sequence. One can also characterize the insert section as including some of the linear primer sequence and its complement. Unless otherwise stated, "insert section" will include the region to which the linear primer initially binds and "linear primer" will include the region that is complementary to the target nucleic acid sequence. Thus, a double extended linear primer that is only a primer dimer, even if it includes nothing more than the random region of the linear primer, can still be characterized as "having" an insert section that is shorter than another double extended linear primer. That is, an "insert section" does not have to include any target nucleic acid sequence and can simply be one or two random regions from the linear primers. As shown in the figures, the hybridization of the linear primer and its complement does not require that the entire linear primer be hybridized to its entire complement, but simply that a part of it (such as the universal region) be hybridized to a part of the complement (such as the universal region complement).

Figure 5:
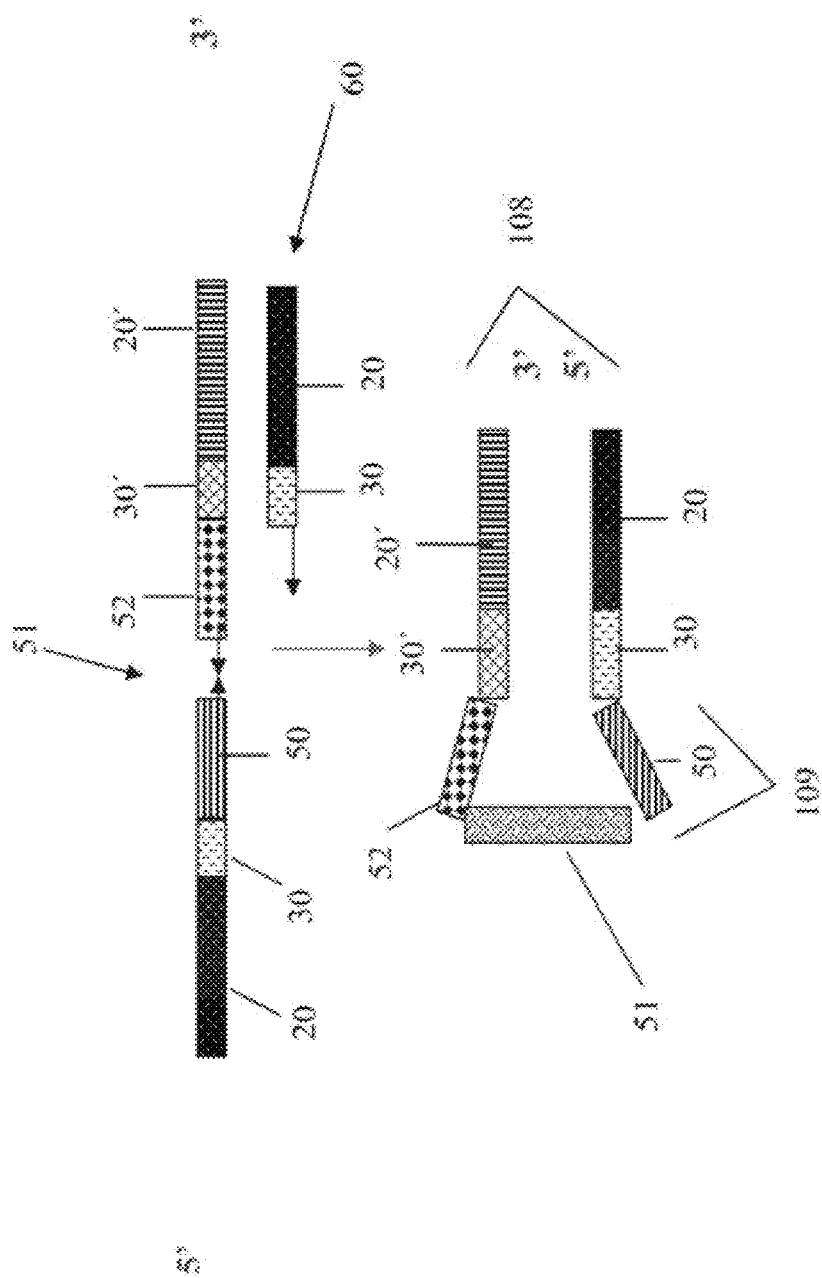
FIG. 5 depicts an embodiment of using a linear primer.

In some embodiments, the insert section 9 can include a significant portion of target nucleic acid sequence, as shown in FIG. 4, which can then be amplified. Alternatively, the insert section can contain an insignificant amount of target DNA 51 (such as when primer dimers occur or overly frequent priming occurs), such an embodiment is shown in FIG. 5. In some embodiments, the insignificant amount of DNA 51 will be no DNA, as such, the insert section is only 50 connected to 52. In other embodiments, a small amount of the target nucleic acid sequence in included 51. In some embodiments, the insert section for the double-extended linear primer to be amplified is between 100 bp and 20 kb nucleotides in length.

The "capture stem" or "insert stem" denotes the section of the double-extended linear primer that is self-hybridized. As will be appreciated by one of skill in the art, when the double extended linear primer is simply a primer dimer, without any additional target nucleic acid sequence, the insert section will comprise the original linear primer sequences. As the structure can still be looped, there can still be unpaired nucleotides within the loop (although there need not be). Such primer dimer formations can be characterized as having an "empty insert section" or "no foreign insert section", as they contain no additional sequence, apart from the starting linear primers; however, as they will still include the 3' target specific regions, there can still be a sequence within the insert section, even though none of it is foreign.

The term "insert amplification primer" refers to a primer that can be used to amplify the insert section. Generally, these primers are complementary to some section of the target nucleic acid sequence that is within the double-extended linear primer. In some embodiments, the insert amplification primers are specific primers with known or knowable sequences. In some embodiments, numerous insert amplification primers will be employed as the specific sequence that has been amplified may not be known. In some embodiments, two or more insert amplification primers are used to amplify the insert sections. In some embodiments, each insert amplification primer (or paired set thereof) will be combined with the double-extended linear primer in a separate reaction chamber (thus the amplified double-extended linear primer will be divided between numerous reaction chambers). In other embodiments, the numerous insert amplification primers and the amplification reaction are performed in a single reaction chamber or are combined in some manner. In some embodiments, the insert amplification primers are degenerate primers. In some embodiments, the insert amplification primers are relatively short to allow for ease of amplification. In some embodiments, the insert amplification primers include universal bases.

The term "intramolecular hybridization" refers to an event or state in which at least a portion of a nucleic acid strand is hybridized to itself.

The terms "self-hybridizing" or "self-hybridized" refer to an event or state in which a portion of a nucleic acid strand is hybridized to another portion of itself. In general, the term is reserved for the effective hybridization of the linear primer to at least a portion of the linear primer complement in a double extended linear primer, e.g., as shown in FIG. 5.

The term "large enough to allow amplification" in reference to the insert section (or capture section) denotes that, relative to other species of sequences in the reaction mixture, the larger size of the insert section of the described species allows for greater or more efficient amplification. If an insert section has a "significant portion of target DNA" it will be large enough to allow amplification. In some embodiments, the insert section is between 200 bp and 10 kb or more nucleic acids in length. In some embodiments, the relative prevention of amplification is between a primer dimer (which comprises only the sequence of the linear primer, e.g., a primer dimer) and a double extended linear primer that includes at least one nucleotide in addition to the linear primer.

The term "short enough to reduce the likelihood that amplification will occur" in reference to the insert section denotes that, relative to other species of sequences in the reaction mixture, the smaller size of the insert of the described species results in less and/or less efficient amplification compared to another species in the reaction mixture. If an insert has "an insignificant amount of target DNA" it is small enough to prevent or reduce the likelihood of amplification of DNA within the insert. In some embodiments, an insert that is short enough to reduce the likelihood that amplification will occur is between 1 and 200 nucleotides in length. As will be appreciated by one of skill in the art, as the linear primer and primer complement can include a 3' target specific region some amount of a target nucleic acid sequence can be present, even in situations where simple primer dimerization has occurred. In some embodiments, these two terms are defined relative to one another. As will be appreciated by one of skill in the art in light of the present disclosure, in some embodiments, the size of the insert section (or insert section) is being used to preferentially reduce the amplification of smaller amplified regions of the target nucleic acid sequence compared to larger target nucleic acid sequences. Thus, in some embodiments, the "prevention" or "reduction" of the amplification of a first double-extended linear primer over a second double-extended linear primer results from the fact that the first has a shorter insert section compared to the second. In some embodiments, any difference in size of the insert section can result in the desired "reduction" or selective amplification, for example, the first double extended can be 99-90, 90-80, 80-70, 70-60, 60-50, 50-40, 40-30, 30-20, 20-10, 10-5, 5-1, 1-0.1, 0.1-0.001% or less the size of the insert section in the second double-extended linear primer.

In some embodiments, relative prevention is between designated larger and smaller sections (or inserts). In some embodiments, the relative prevention or reduction in likelihood is in comparison to the same sequence as the insert sequence, except that the sequence is not looped (e.g., same insert sections sequence, but no or insignificant amounts of the stem forming region). In some embodiments, the relative prevention is between a primer dimer (which comprises only the sequence of the linear primer, e.g., a primer dimer) and a double extended linear primer that includes at least one nucleotide in addition to the linear primer. In some embodiments, the prevention or reduction is specific to the prevention of the amplification of primer dimers.

As will be appreciated by one of skill in the art, in embodiments in which one is amplifying within a self-hybridized structure, at large enough lengths, the amplification in the insert section does not change significantly upon increasing the length of the nucleic acid sequence in the insert section. However, these sequences can still be preferentially amplified over double-extended linear primers having shorter length insert sections. As noted below, in some embodiments, insert sections of at least 100 bp are generally used in order to have amplification within the in the loop or insert section. In embodiments in which SNP genotyping and gene dosage RT-PCR are employed, the length of the inserts can be 100 bp pr longer, in order to allow spacing for two primers and probes (e.g., TAQMAN® probes). For some embodiments, such as capillary electrophoresis for sequencing applications, the insert sections can be 500 bp or longer. Insert sections of at least 500 bp can result in very efficient amplification in the loop. If longer loops are desired, the annealing time and/or extension time can be increased during PCR. In embodiments in which a self-hybridized structure is not formed for the longer double extended linear primer, then there need be no minimal size, as long as it is longer than the other double extended linear primer that the long double extended linear primer is to be amplified over.

As used herein, the term "identifying portion" refers to a moiety or moieties that can be used to identify a particular linear primer species, and can refer to a variety of distinguishable moieties including zipcodes, a known number of nucleobases, and combinations thereof. In some embodiments, an identifying portion, or an identifying portion complement, can hybridize to a detector probe, thereby allowing detection of a target nucleic acid sequence in a decoding reaction. The terms "identifying portion complement" typically refers to at least one oligonucleotide that comprises at least one sequence of nucleobases that are at least substantially complementary to and hybridize with their corresponding identifying portion. In some embodiments, identifying portion complements serve as capture moieties for attaching at least one identifier portion and target nucleic acid sequence to at least one substrate; serve as "pull-out" sequences for bulk separation procedures; or both as capture moieties and as pull-out sequences (see for example O'Neil, et al., U.S. Pat. Nos. 6,638,760, 6,514,699, 6,146,511, and 6,124,092).

Typically, identifying portions and their corresponding identifying portion complements are selected to minimize: internal, self-hybridization; cross-hybridization with different identifying portion species, nucleotide sequences in a reaction composition, including but not limited to gDNA, different species of identifying portion complements, or target-specific portions of probes, and the like; but should be amenable to facile hybridization between the identifying portion and its corresponding identifying portion complement. Identifying portion sequences and identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

In some embodiments, the detector probe can hybridize to both the identifying portion as well as sequence corresponding to the target nucleic acid sequence. In some embodiments, at least two identifying portion-identifying portion complement duplexes have melting temperatures that fall within a $\Delta T_m$ range ($T_{max}-T_{min}$) of no more than 10° C. of each other. In some embodiments, at least two identifying portion-identifying portion complement duplexes have melting temperatures that fall within a $\Delta T_m$ range of 5° C. or less of each other. In some embodiments, at least two identifying portion-identifying portion complement duplexes have melting temperatures that fall within a $\Delta T_m$ range of 2° C. or less of each other.

In some embodiments, at least one identifying portion or at least one identifying portion complement is used to separate the element to which it is bound from at least one other component of a ligation reaction composition, a digestion reaction composition, an amplified ligation reaction composition, or the like. In some embodiments, identifying portions are used to attach at least one ligation product, at least one ligation product surrogate, or combinations thereof, to at least one substrate. In some embodiments, at least one ligation product, at least one ligation product surrogate, or combinations thereof, comprise the same identifying portion. Examples of separation approaches include but are not limited to, separating a multiplicity of different element-identifying portion species using the same identifying portion complement, tethering a multiplicity of different element-identifying portion species to a substrate comprising the same identifying portion complement, or both. In some embodiments, at least one identifying portion complement comprises at least one label, at least one mobility modifier, at least one label binding portion, or combinations thereof. In some embodiments, at least one identifying portion complement is annealed to at least one corresponding identifying portion and, subsequently, at least part of that identifying portion complement is released and detected, see for example Published P.C.T. Application WO04/4634 to Rosenblum et al., and Published P.C.T. Application WO01/92579 to Wenz et al.

As will be appreciated by one of skill in the art, while the presently disclosed linear primers can include an identifying portion, it need not be included and is not included in some embodiments. In some embodiments, the linear primer includes an identifying portion as well as the noncomplementary region. Is some embodiments, the identifying portion is not the same as the noncomplementary region. In some embodiments, an identifying portion is not included in a linear primer.

As used herein, the term "extension reaction" refers to an elongation reaction in which the 3' target specific portion of a linear primer is extended to form an extension reaction product comprising a strand complementary to a target nucleic acid sequence. In some embodiments, the target nucleic acid sequence is a gDNA molecule or fragment thereof. In some embodiments, the target nucleic acid sequence is a short DNA molecule and the extension reaction comprises a polymerase and results in the synthesis of a $2^{nd}$ strand of DNA. In some embodiments, the consolidation of the extension reaction and a subsequent amplification reaction is further contemplated by the present teachings.

As used herein, the term "primer portion" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer portions are present on a single polynucleotide, the orientation of the two primer portions is generally different. For example, one PCR primer can directly hybridize to a first primer portion, while another PCR primer can hybridize to the complement of the second primer portion. In some embodiments, "universal" primers and primer portions as used herein are generally chosen to be as unique as possible given the particular assays and sequences involved to ensure specificity of the assay. However, as will be appreciated by one of skill in the art, when a noncomplementary region is employed, the need for uniqueness with regard to the universal priming region is greatly diminished if not removed completely.

Figure 7:
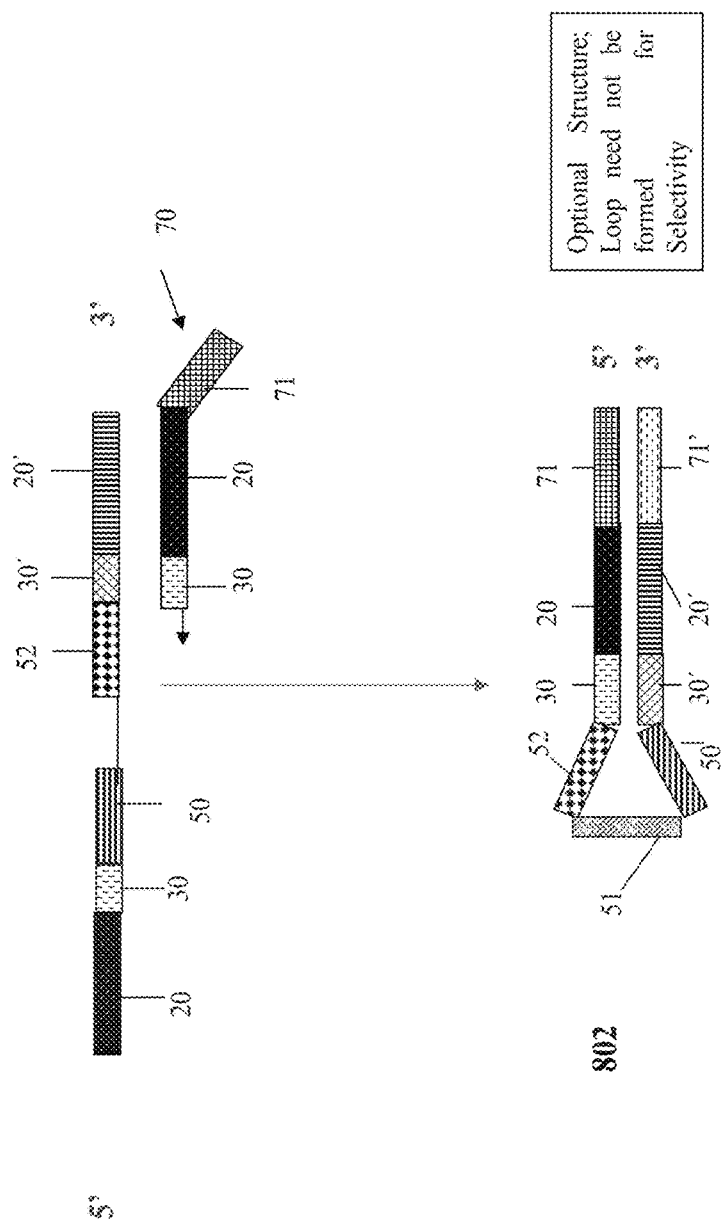
FIG. 7 depicts an embodiment of using a linear primer.

The term "tail region" of a primer denotes a section at the 5' end of a primer sequence. In some embodiments this section can hybridize to part of a target sequence or priming site (e.g., such that the entire primer is hybridized to a target sequence or priming site). In some embodiments, the tail region has a sequence that is not complementary to the nucleic acid sequence that the remaining portion of the primer has hybridized to (e.g., the 5' end is not hybridized to a priming site while the rest of the primer can hybridize). In some embodiments, primers having different tail regions are used so as to allow for a sequence difference to be made at each end of the nucleic acid sequence (e.g., as shown in FIG. 7). Such a tail region can be denoted as a "noncomplementary tail region" or a second tail region, wherein the second tail region is different from the first. In some embodiments, the tail portion can include a zip-code, which can allow for the identification or tracking of the molecule associated with the zip-code. In some embodiments, the tail portion of the forward primer is between 5-8 nucleotides long. As will be appreciated by one of skill in the art, the length of the tail can determine the stability of the stem loop. If primer dimers are not a significant problem, the tail can be, for example, as large as a 20-mer to allow for the incorporation of forward and reverse primers for sequencing reactions that require two different primers. In some embodiments, one can reduce potential primer-dimer formation from carry over random primers by using tails that are less than 5-8 nucleotides in length. In some embodiments, a noncomplementary tail region is not used.

In some embodiments, the tail portion of the forward primer is 6 nucleotides long. Those in the art will appreciate that forward primer tail portion lengths shorter than 5 nucleotides and longer than 8 nucleotides can be identified in the course of routine methodology and without undue experimentation, and that such shorter and longer forward primer tail portion lengths are contemplated by the present teachings.

The term "upstream" as used herein takes on its customary meaning in molecular biology, and refers to the location of a region of a polynucleotide that is on the 5' side of a "downstream" region. Correspondingly, the term "downstream" refers to the location of a region of a polynucleotide that is on the 3' side of an "upstream" region.

As used herein, the term "hybridization" refers to the complementary base-pairing interaction of one nucleic acid with another nucleic acid that results in formation of a duplex, triplex, or other higher-ordered structure, and is used herein interchangeably with "annealing." Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementarity, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that the probes or primers are sufficiently complementary to the target sequence to hybridize under the selected reaction conditions to achieve the ends of the present teachings. Something is "configured to hybridize" when its sequence (e.g., structure) allows hybridization through base specific, e.g., A/T and G/C, by Watson/Crick and Hoogsteen-type hydrogen bonding.

As used herein, the term "amplifying" refers to any method by which at least a part of a target nucleic acid sequence, target nucleic acid sequence surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, 3.sup.rd Edition; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 February; 13(2):294-307, and Landegren et al., Science 241:1077-80 (1988), Demidov, V., Expert Rev Mol Diagn. 2002 November; 2(6):542-8, Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a linear primer that is annealed to a template in the 5' to 3' direction using an amplifying means such as a polymerase and/or reverse transcriptase.

According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed linear primer, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2).

In some embodiments of the present teachings, any of a variety of techniques can be employed prior to amplification in order to facilitate amplification success, as described for example in Radstrom et al., Mol Biotechnol. 2004 February; 26(2):13346. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536,649, and U.S. Provisional Application 60/584,682 to Andersen et al.). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

As used herein, the term "detector probe" refers to a molecule used in an amplification reaction, typically for quantitative or real-time PCR analysis, as well as end-point analysis. Such detector probes can be used to monitor the amplification of the target nucleic acid sequence. In some embodiments, detector probes present in an amplification reaction are suitable for monitoring the amount of amplicon(s) produced as a function of time. Such detector probes include, but are not limited to, the 5'-exonuclease assay (TAQMAN® probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor™ probes (U.S. Pat. No. 6,548,250), stem-loop and duplex Scorpion probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescenin dyes with $SO_3$ instead of the carboxylate group, phosphoramidite forms of fluorescein, phosphoramidite forms of CY 5 (commercially available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69° C., though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements.

The term "corresponding" as used herein refers to a specific relationship between the elements to which the term refers. Some non-limiting examples of corresponding include: a linear primer can correspond with a target nucleic acid sequence, and vice versa. A forward primer can correspond with a target nucleic acid sequence, and vice versa. In some cases, the corresponding elements can be complementary. In some cases, the corresponding elements are not complementary to each other, but one element can be complementary to the complement of another element.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "reaction vessel" or "reaction chamber" generally refers to any container in which a reaction can occur in accordance with the present teachings. In some embodiments, a reaction vessel can be an eppendorf tube or other container of the sort in common use in modern molecular biology laboratories. In some embodiments, a reaction vessel can be a well in a microtitre plate, a spot on a glass slide, or a well in an Applied Biosystems TaqMan Low Density Array for gene expression (formerly MicroCard™). A plurality of reaction vessels can reside on the same support. In some embodiments, lab-on-a-chip like devices, available for example from Caliper and Fluidgm, can provide for reaction vessels. In some embodiments, various microfluidic approaches as described in U.S. Provisional Application 60/545,674 to Wenz et al., can be employed. It will be recognized that a variety of reaction vessels are available in the art and within the scope of the present teachings.

As used herein, the term "detection" refers to a way of determining the presence and/or quantity and/or identity of a target nucleic acid sequence. In some embodiments the sequence to be detected is known. Thus, in some embodiments, detection occurs by determining if the target nucleic acid sequence comprises or consists of a known nucleic acid sequence, gene, etc. In some embodiments, the sequence to be detected is not known prior to the experiment. In such embodiments, the target nucleic acid sequence is amplified and sequenced. The sequencing of the target nucleic acid can be characterized as "detecting" the target nucleic acid. The target nucleic acid sequence to be sequenced can be known or unknown prior to its sequencing. Thus, in some embodiments, a target nucleic acid is sequenced to determine if a specific sequence or gene is present in a sample, and/or determine what specific variant is present. In some embodiments, a target nucleic acid is sequenced to determine the sequences of the genes or nucleic acid sequences themselves (e.g., the sequence and/or identity of the target nucleic acid sequence is not known prior to sequencing).

In some embodiments employing a donor moiety and signal moiety, one can use certain energy-transfer fluorescent dyes for detection. Certain nonlimiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, VIC®, LIZ®, TAMRA™ (carboxytetramethylrhodamine, succinimidyl ester), 5-FAM™ (5-carboxyfluorescein), 6-FAM™ (6-carboxyfluorescein), and Texas Red (Molecular Probes). (VIC®, LIZ®, TAMRA™, 5-FAM™, and 6-FAM™ all available from Applied Biosystems, Foster City, Calif.).

In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator.

According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), and the ABI GeneAmp® 7500 Sequence Detection System (Applied Biosystems). In some embodiments, each of these functions can be performed by separate devices. For example, if one employs a Q-beta replicase reaction for amplification, the reaction does not need to take place in a thermal cycler, but could include a light beam emitted at a specific wavelength, detection of the fluorescent signal, and calculation and display of the amount of amplification product. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification.

In some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid sequence. As used herein, determining the presence of a target can comprise identifying it, as well as optionally quantifying it. In some embodiments, the amplification products can be scored as positive or negative as soon as a given number of cycles is complete. In some embodiments, the results can be transmitted electronically directly to a database and tabulated. Thus, in some embodiments, large numbers of samples can be processed and analyzed with less time and labor when such an instrument is used.

In some embodiments, different detector probes can distinguish between different target nucleic acid sequences. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different stem regions of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' can form even if the appropriate target nucleic acid sequence is not in the sample, but such occurs to a measurably lesser extent than when the appropriate target nucleic acid sequence is in the sample. After amplification, one can determine which specific target nucleic acid sequences are present in the sample based on the wavelength of signal detected and their intensity. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B.

In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target nucleic acid sequence determined via a mobility dependent analysis technique of the eluted mobility probes, as described for example in Published P.C.T. Application WO04/46344 to Rosenblum et al., and WO01/92579 to Wenz et al. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:14045, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

The term "anneal" as used herein refer to the base-pairing interaction of one polynucleotide with another polynucleotide that results in the formation of a duplex or other higher-ordered structure. The primary interaction is base specific, i.e., A/T and G/C, by Watson/Crick and Hoogsteen-type hydrogen bonding.

The term "real-time analysis" refers to periodic monitoring during PCR. Certain systems such as the ABI 7700 and 7900HT Sequence Detection Systems (Applied Biosystems, Foster City, Calif.) conduct monitoring during each thermal cycle at a predetermined or user-defined point. Real-time analysis of PCR with FRET probes measures fluorescent dye signal changes from cycle-to-cycle, preferably minus any internal control signals.

The term "5'-nuclease analysis" or "5'-nuclease assay" when used herein refers to "real-time analysis" for quantification of the amount of DNA amplified in a particular PCR reaction. TAQMAN® analysis is an example of such "5'-nuclease analysis" (a commercially available PCR kit). "5'-nuclease analysis" involves the use of a fluorogenic oligonucleotide probe to which a reporter dye and a quencher dye are attached. During amplification of a nucleotide sequence using a forward and reverse primer, the probe anneals to the target of interest between the forward and reverse primer sites. During extension, the probe is cleaved by the 5'-nuclease activity of the DNA polymerase. As the cleavage separates the reporter dye from the quencher dye, the reporter dye's fluorescence increases which can be detected and quantitated. Real-time analysis of PCR with 5'-nuclease assay involves FRET probes that can be displayed by plotting the logarithmic change in detected fluorescence (ΔRn) versus the cycle number. The cycle within the PCR protocol at which the change in fluorescence (ΔRn) rises above a threshold value is denoted as $C_T$. The $C_T$ cycle is approximately the cycle at which amplification of target becomes exponential. A relatively low $C_T$ value indicates efficient detection of amplicon. The threshold cycle is highly correlated to the amount of copy number, or amount of target nucleic acid sequence present in the sample, as well as the efficiency of amplification. The effects of primer constitution, e.g. length, sequence, mismatches, analogs, can be conveniently screened and quantitated by measurement of $C_T$ values during real-time analysis of PCR. In some embodiments, the sequences within the insert sections can be detected and/or amplified via a TAQMAN® assay or similar assay.

"Polymerase chain reaction" or "PCR" as used herein, refers to a method in the art for amplification of a nucleic acid. The method can involve introducing a molar excess of two or more extendable oligonucleotide primers to a reaction mixture comprising the desired target sequence(s), where the primers hybridize to opposite strands of the double stranded target sequence. The reaction mixture is subjected to a program of thermal cycling in the presence of a DNA polymerase, resulting in the amplification of the desired target sequence flanked by the oligonucleotide primers. The oligonucleotide primers prime multiple sequential rounds of DNA synthesis, each round of synthesis is typically separated by a melting and re-annealing step. Methods for a wide variety of PCR applications are widely known in the art, and are described in many sources, for example, Ausubel et al. (eds.), Current Protocols in Molecular Biology, Section 15, John Wiley & Sons, Inc., New York (1994).

"In silico PCR" when used herein refers to a computer-conducted method for predicting the size and probability of amplification of a nucleotide sequence using a particular set of primers. The method involves searching a DNA database for exact matches to the primer sequences and further for sequences having the correct order, orientation, and spacing to allow priming of amplification of a nucleotide sequence of a predicted size.

"Tm" as used herein, refers to the melting temperature (temperature at which 50% of the oligonucleotide is a duplex) of the oligonucleotide calculated using the nearest-neighbor thermodynamic values of Breslauer et al. (Proc. Natl. Acad. Sci. USA 83:3746 3750, 1986) for DNA and Freier et al. (Proc. Natl. Acad. Sci. USA 83:9373 9377, 1986) for RNA.

As will be appreciated by one of skill in the art, the above definitions occasionally describe various embodiments that can also be used, in some embodiments, with the variously defined parts or steps. Unless indicated, these various embodiments are not required or part of the actual definitions and have been included for additional general context and for further description of the various contemplated embodiments.

Aspects of the present teachings can be further understood in light of the following description and examples, which should not be construed as limiting the scope of the present teachings in any way.

Linear Primers and Uses Thereof

There are numerous strategies for nucleic acid amplification involving the use of random or degenerate primers. These primers can be especially useful in the amplification of unknown sequences, such as in whole genome amplification. To date, many of the techniques have drawbacks, including issues such as primer-dimer formation or the accumulation of other relatively short fragment artifacts that dominate PCR or other amplification procedures. In addition, the ability to prime from larger sections of gDNA (e.g., so as to avoid over processing of the gDNA) faces various difficulties in that previous techniques were biased to priming at the ends of the strand, thus leaving much of the internal sequences of these larger sections of gDNA target less examined or amplified.

In some embodiments, some or all of the above issue(s) can be addressed by using linear primers to prime the target nucleic acid. In some embodiments, these linear primers include a random or degenerate priming sequence (or more generally 3' target specific regions), a universal priming region (or universal priming section) and optionally a non-complementary region. Such an arrangement can produce a product that can then be amplified with a reduced likelihood of forming primer-dimers and/or other nonspecific priming events.

Figure 1B:
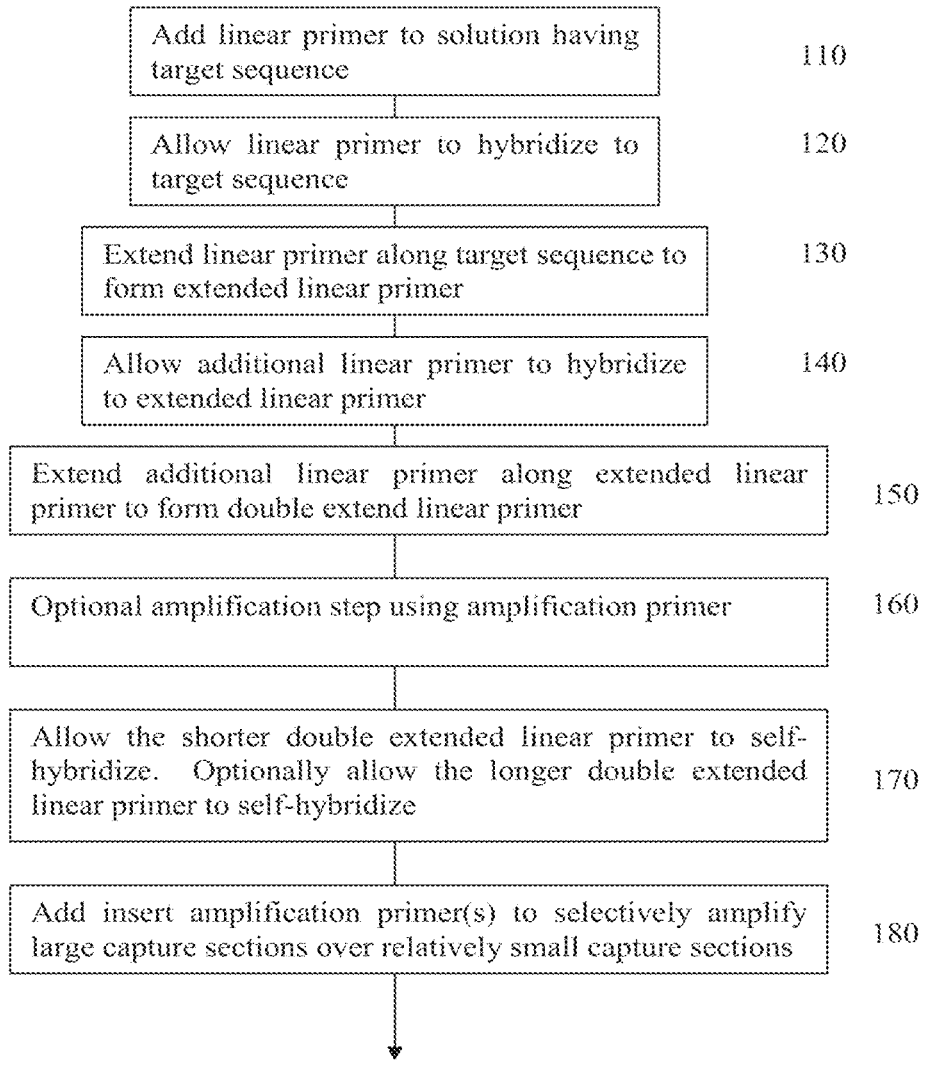
FIG. 1B is a flow chart depicting one embodiment using a linear primer to produce a self-hybridizing nucleic acid sequence.

FIGS. 1A and 1B depict one embodiment of a linear primer 6 and an embodiment of its use. The linear primer can include a 3' target specific region 50, a universal priming region 20, and optionally a noncomplementary region 30.

The optional noncomplementary region 30 can have various advantages in various embodiments. For example, by selecting a noncomplementary region that is relatively rare in the middle of gDNA (such as a poly T sequence), one can reduce the likelihood that spurious internal priming will occur in various amplification steps. Additionally, when various universal regions are employed, the presence of the noncomplementary region (which can be the same across all of the linear primers) can reduce the likelihood that primer-dimers will form.

As described in detail below, and outlined in FIG. 1B, in some embodiments, the linear primer can be used to initiate priming as desired (e.g., via a random or degenerate priming region), while still including a universal and a noncomplementary region in the primer. Moreover, this can be achieved with a reduced risk of nonspecific or primer-dimer interactions occurring.

In some embodiments, such as the one depicted in FIG. 1B, the use of the linear primer to amplify sections of a target sequence allows one to place complementary sequences on either end of the amplified target nucleic acid sequence. As noted below, the addition of these complementary sequences allow for the size dependent amplification of the target nucleic acid sequences.

The first step depicted in FIG. 1B is the addition of a linear primer (6 depicted in FIG. 1A) to a solution that includes the target nucleic acid sequence or sequences that are to be amplified 110 or in which a target is to be identified, if present. Conditions are selected such that the linear primer hybridizes to the target sequence 120. The linear primer is then extended along the target sequence to form an extended linear primer 130. One can then allow a linear primer (the same degenerate linear primer, an identical linear primer, or a different linear primer, as long as the same universal priming region is present) to hybridize to the extended linear primer 140. Then one can extend the linear primer along the extended linear primer to form a double-extended linear primer 150. In various embodiments, the linear primers can have identical sequences; can have identical sequences apart from the 3' target specific region; can have different sequences, apart from the noncomplementary region; or can have different sequences.

In some embodiments, some or all of steps 110-150 can be repeated as desired. In some embodiments, some or all of steps 110-150 can be repeated as desired prior to proceeding to step 160. Following step 150, one can optionally amplify the double-extended linear primer using an amplification primer 160. The amplification primer will have a sequence that will hybridize to a sequence that is complementary to the universal priming region on the primer (e.g., the amplification primer can have a sequence that is or is a part of the universal priming region) and optionally (if necessary) a sequence that will hybridize to the noncomplementary region. As will be appreciated by one of skill in the art, in some embodiments, only one of these regions will be present.

One can then allow the shorter double-extended linear primer to self-hybridize 170. In some embodiments, one can allow both the short and the long double-extended linear primers to self-hybridize. This self-hybridized population can then be used in the selective amplification of large insert sections over relatively small insert sections 180 (depicted in FIGS. 4 and 5). Thus, in some embodiments, the use of the linear primer described above results in a self-hybridized population that allows for the selective amplification of larger sections of target nucleic acid sequences over smaller sections of target nucleic acid sequences contained within the self-hybridized structures. In some embodiments an initial reverse transcription step can be performed or a cleaning step can be included, for example as described in the following sections.

While the self-hybridized structure can be used to help select larger insert section (or insert sections) over smaller insert sections, the larger double extended linear primer need not assume a looped configuration. For example, in some embodiments, the self-hybridized structure is only formed for the shorter insert sections. Thus, in some embodiments, selective amplification of longer insert sections over shorter insert sections (including primer dimers) occurs without the formation of a self-hybridized structure for the longer double extended linear primer. Without intending to be limited by theory, it is understood that because a shorter insert sections will mean that there is less distance between the linear primer and the linear primer complement, that these short double extended linear primers will self hybridize faster than double extended linear primers with larger insert sections. Similarly, the larger double-extended linear primers will have more distance between the linear primer and its complement and thus it can take longer for the primer and its complement to self-hybridize. Thus, in some embodiments, it is the faster ability of the double extended linear primers having shorter insert sections to self-hybridize, and thus take themselves out of a reaction, that allows for the selective amplification of the double extended linear primers having the longer insert sections over the shorter (or no foreign) insert sections. Thus, in some embodiments, the longer or long insert section is not in a looped configuration during the selective amplification.

Figure 1C:
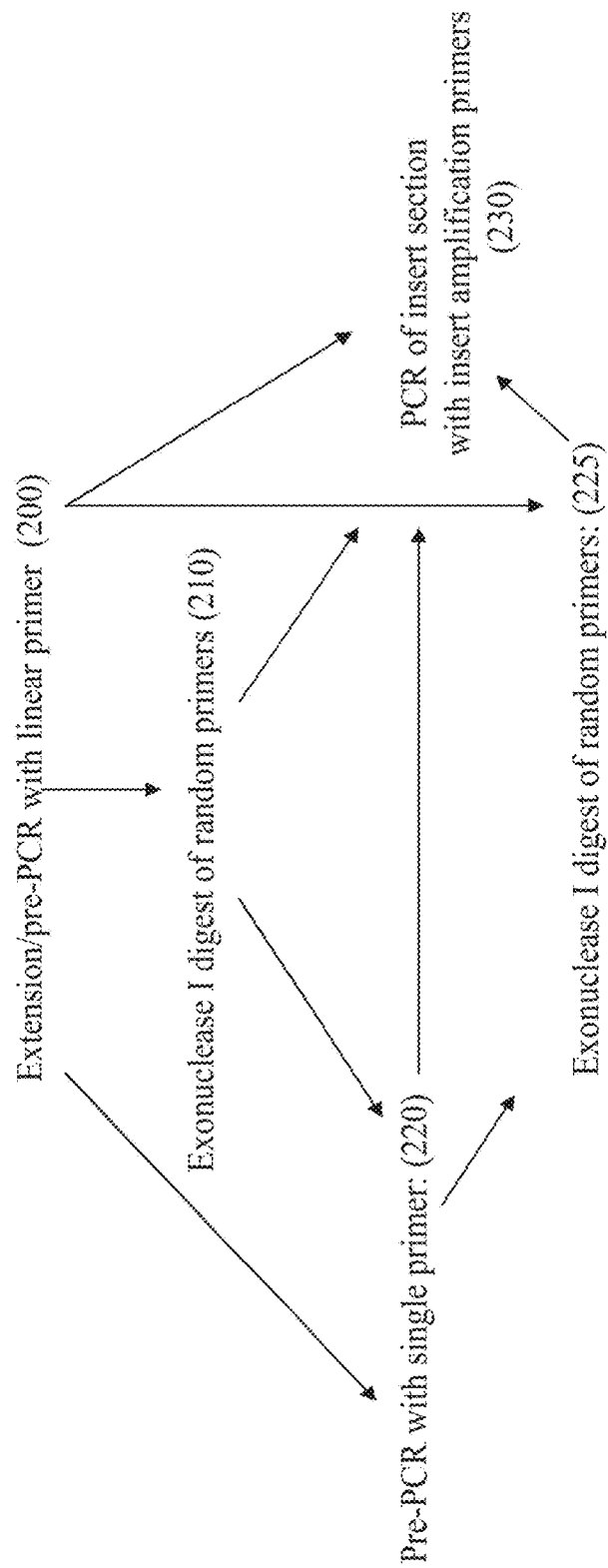
FIG. 1C is a flow chart depicting some embodiments involving a linear primer.

Additional embodiments of the method of using the linear primers for the selective amplification of relatively larger target nucleic acid sequences (compared to shorter target nucleic acid sequences) are shown generally in FIG. 1C. The first step 200 can involve primer extension via the linear primers described above (to form a double-extended linear primer) which can be followed by step 210, a digestion of various random primers, such as with exonuclease I. In some embodiments, this is followed by a pre-PCR amplification step with a single amplification primer (step 220). Following this, a step is performed to amplify the insert section, depending upon the size of the target nucleic acid sequence within the insert section. This can be achieved with an insert amplification primer (step 230). As shown in FIG. 1C by the arrows, various steps can be included or removed for various embodiments. In some embodiments, the cleaning step 225 is not performed or is performed after the pre-PCR amplification 220. In some embodiments, multiple rounds of cleaning (e.g., exonuclease digestion) are employed. Specific embodiments involved in these methods are discussed in more detail in regard to FIGS. 2-7.

Figure 2:
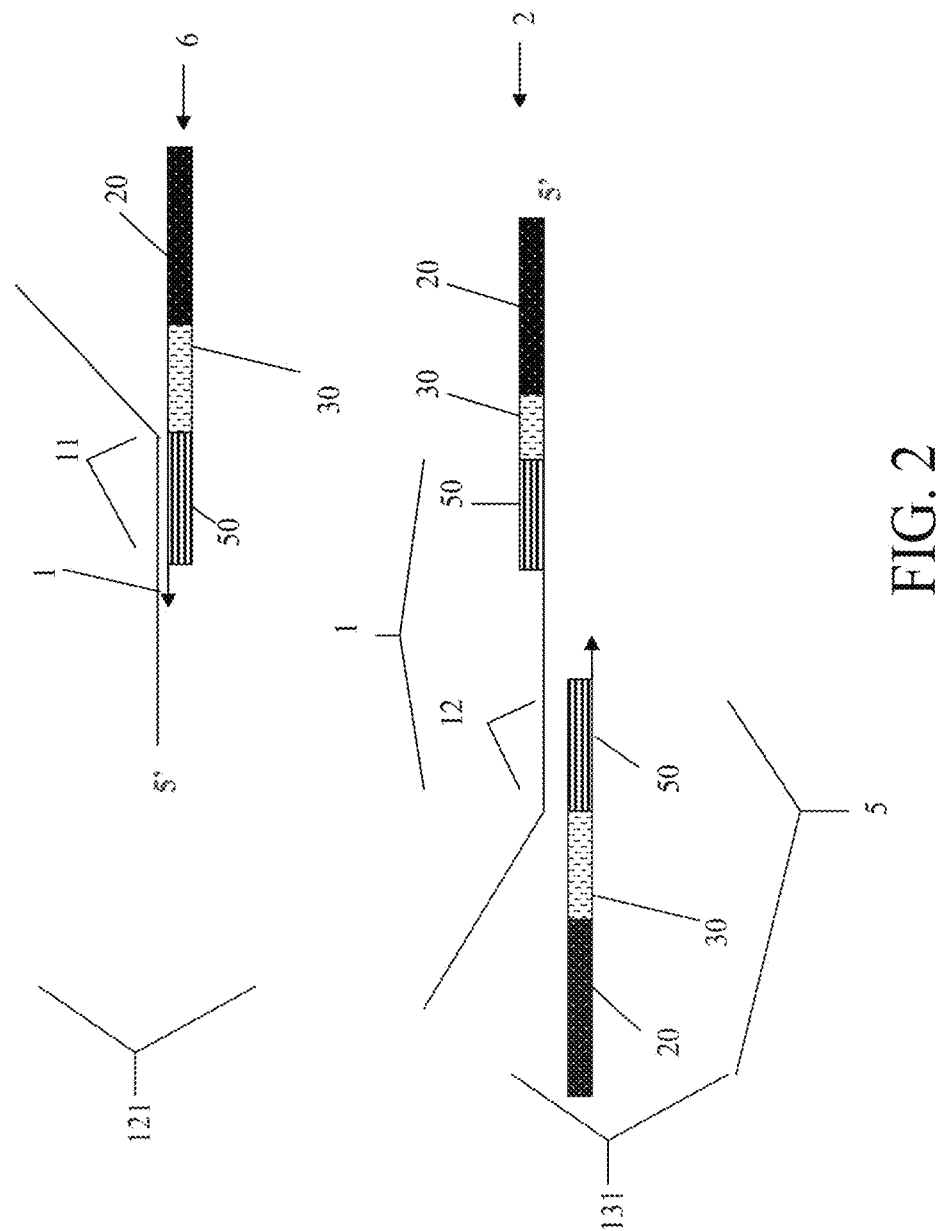
FIG. 2 depicts an embodiment of using a linear primer.

In the top section of FIG. 2, the linear primer 6 is shown hybridized at a first part 11 at a complementary portion of the target nucleic acid sequence 1 in a first arrangement 121. This results from a first step in which the linear primer 6 is allowed to anneal via the 3' target specific region 50 to the first part of the target nucleic acid sequence at a target binding site 11. Following the hybridization, the primer is extended along the target sequence in the 5' direction of the target sequence or in the 3' direction from the linear primer (arrow). Following this extension, an additional linear primer 5 (which can have the same sequence as the first linear primer, a different sequence (but same universal priming region 20 and/or noncomplementary region 30), and/or the same 3' target specific region 50 and/or universal priming region 20) hybridizes at a complementary portion of the extended linear primer 2 at a second target binding site 12, as shown in FIG. 2, in a second arrangement 131. As above, the linear primer 6 can include a 3' specific target region 50, optionally a noncomplementary region 30, and a universal priming region 20. In some embodiments, the linear primers 5 and 6 are the same. In some embodiments, the linear primers are the same, apart from their 3' target specific region 50.

In some embodiments, the 3' target specific region is a degenerate region; thus, identifier "50" can represent multiple or different sequences on different primers as it can be a degenerate sequence. For FIGS. 3-7, the 3' target specific region is depicted as identifier 50 and 52, (to provide additional clarity for some embodiments in which the 3' target specific region is degenerate), and thus the specific sequences of 50 and 52 are identified by different identifiers in the figures. However, both 50 and 52 can be a 3' target specific region (and thus can be the same in some embodiments). In addition, the 3' target specific region identifier "50" can be used generically throughout a single figure (such as in FIG. 8), to denote different sequences, even though a single identifier is used (thus, "50" and "52" need not be present to denote that a region is degenerate). One of skill in the art will readily appreciate how this and other sequences within these linear primers 5 & 6 can be differed, if desired.

Following the hybridization of the linear primer 6 to the extended linear primer 2 the linear primer 6 is extended from its 3' direction to the 5' direction of the extended linear primer. This extension results in a double-extended linear primer 4 (FIG. 3). As noted above, the term "double-extended linear primer" does not imply that the sequence functions as a primer, but that it is formed from extending linear primers.

The double-extended linear primer can optionally be amplified at this point. This is shown in more detail in FIG. 3 in which an amplification primer 60 is used to amplify the double-extended linear primer 4. In some embodiments, the amplification primer includes, comprises, consists, or consists essentially of the universal priming region 20. In some embodiments, the amplification primer includes the non-complementary region 30 and/or a sequence that is the same as the original universal region 20. This first amplification primer 60 can hybridize to the double-extended linear primer 4 allowing for efficient amplification of the double-extended linear primer. In some embodiments, more than one amplification primer can be used. In some embodiments, only a single primer per linear primer nucleic acid sequence is used in the amplification step depicted in FIG. 3. In some embodiments, the use of a single primer sequence that will not hybridize to the initial linear primer can help reduce nonspecific primer dimerization that could otherwise occur due to the presence of an amplification primer and remaining linear primers. Thus, by selecting an amplification primer that has the same sequence as a portion of the linear primer, one can further reduce the risk of primer dimerization or other nondesired hybridization events. Of course, the presence of the noncomplementary region 30 in the linear primer 6 can be exploited in selecting such an amplification primer 60. In some embodiments, the amplification of the double extended linear primer results in the selective amplification of double extended linear primers having long insert sections over those with shorter or no insert sections.

As will be appreciated by one of skill in the art, the amplification step can occur in situations in which additional background DNA or nucleic acid sequences are present. As will be appreciated by one of skill in the art, in embodiments in which the linear amplification primer only hybridizes to the universal priming region, there could be significant priming events to non target sections. However, the presence of the noncomplementary region in the linear primer (and more specifically sequences complementary to these regions in the double-extended linear primer) and in the amplification primer reduce the likelihood that this will occur.

Following the optional amplification step, at least a subpopulation of the double-extended linear primer can self-hybridize (as shown in FIG. 5). As noted above, self-hybridization of the double extended linear primer does not have to occur for all species in a sample. Rather, self-hybridization need only occur for the shorter sequences (FIG. 5) which are to be reduced or amplified over. Thus, in some embodiments, self-hybridization occurs for the structures in FIG. 5, but not for the structures depicted in FIG. 4. However, in some embodiments, the longer double-extended linear primers also self-hybridize, as shown in FIG. 4.

As will be appreciated by one of skill in the art, the portions of the double-extended linear primer corresponding to the universal priming region 20 and the universal priming region complement 20' are capable of hybridizing to one another. The insert section 9 itself can then have the target nucleic acid sequence, or fragment thereof, which can be amplified by any of various reactions such as PCR. In some embodiments, insert amplification primer(s) 80 and/or 81 are used to amplify at least a portion of the insert section. As will be appreciated by one of skill in the art, in some embodiments, the size of the insert section should be sufficient to allow amplification.

In embodiments in which self-hybridization of the longer double extended linear primers is not required to occur (e.g., does not occur frequently or is not driving a subsequent selective amplification of longer insert sections over shorter insert sections), then the selective amplification is believed to occur due to the fact that the shorter double-extended linear primers self-hybridize more rapidly than the longer double-extended linear primers and thus are removed from subsequent rounds of amplification more quickly than the longer double-extended linear primers. In such embodiments, while self-hybridization still occurs for the shorter double-extended linear primers (e.g., primer dimers) it does not need to occur for the longer double-extended linear primers. As the linear primer and the linear primer complement on these longer double-extended linear primers (as depicted in FIG. 4) are separated by more nucleotides than the shorter double-extended linear primer (FIG. 5), the self-hybridization of the longer double-extended linear primers will take longer, allowing more time for the insert amplification primer to hybridize and extend. Thus, the self-hybridized structure for the longer double-extended linear primer need not be formed to selectively amplify the longer double-extended linear primer over the shorter double-extended linear primer.

As will be appreciated by one of skill in the art, in embodiments in which whole genome amplification is being performed, the precise sequence within the insert section can be unknown. In light of this, it can be advantageous to use multiple insert amplification primers to make certain that one will prime and extend as desired. In some embodiments, a pool of insert amplification primers is used. In other embodiments, one insert amplification primer (and/or one set or more) is mixed with the solution containing the double-extended linear primer. As will be appreciated by one of skill in the art, numerous such mixtures (e.g., 2-10, 10-100, 100-1,000, 1,000-10,000 or more) can be done in series or in parallel. Furthermore, the solution containing the double-extended linear primer can be divided into parts so that the various reactions can be run in parallel.

As will be appreciated by one of skill in the art, not every linear primer will necessarily hybridize to the target sequence as desired and in some embodiments a linear primer duplex or primer dimer will be formed. Additionally, in some embodiments, linear primers can hybridize to one another, also forming short amplification products. Additionally, in some embodiments, nonspecific hybridization or overly frequent hybridization of the 3' target specific region or of other sections (such as the universal priming region) of the various primers to sections of the target nucleic acid sequence can occur such that only these smaller sections of the target nucleic acid sequence are amplified. One depiction of the above is shown in FIG. 5. In such a situation, rather than having target nucleic acid sequence (or a significant amount of it) between the universal priming region 20 and the complement to the universal priming region 20', there is an insignificant amount of target sequence between the two 20 and 20'. As shown in FIG. 5, when the universal priming region 20 and linear universal priming region complement 20' hybridize together under this situation, the insert section 109 in the complex 108 is relatively small. In some embodiments, there is a nucleic acid sequence 51 in the insert section between the 3' target specific region 50 and its complement 52. This nucleic acid sequence 51 need not be present and, if it is present, is relatively short. In some embodiments, (when a sufficiently large insert is present) the insert 109 (including sequence 51) is not more than 10 kb in length. In some embodiments, the insert 109, while still capable of allowing amplification does so with relatively less efficiency than the double-extended linear primer complex 8 shown in FIG. 4. As such, relative amplification of the product 8 shown in FIG. 4 can be achieved compared to amplification of the resulting product 108 shown in FIG. 5. As will be appreciated by one of skill in the art, this distinction between the two resulting products can reduce the role or impact that nonspecific primer interactions can have, e.g., primer dimers on the ability to identify amplified sequence target. That is, this distinction can generally improve target detection by reducing the impact of nucleic acid structures (or products) in which a significant or substantial amount of target DNA has not incorporated between the two primers. As will be appreciated by one of skill in the art, when the 3' target specific region 50 and 52 are complementary to one another (e.g., when only a single sequence is used and the 3' target specific region is not a degenerate sequence) they can hybridized together and the sequence 51 need not be present (e.g., when the double-extended linear primer is just a primer dimer). In embodiments in which the 3' target specific region is a degenerate region or sequence, then sections 50 and 52 need not, and often will not, be complementary to one another.

While not depicted in FIGS. 4 and 5, one of skill in the art will readily recognize that in the embodiments in which a self-hybridized structure is not created for the longer double-extended linear primer, that the insert amplification primers 81 and 80 can bind to the "open" double-extended linear primer, and can bind to the universal priming region or other section of the linear primer. In some embodiments, one of the insert amplification primers comprises, consists, or consists essentially of a universal priming region, while the second insert amplification primer primes in the insert. In some embodiments, both insert amplification primers hybridize within the insert (as shown in FIG. 4, although no actual loop need be formed). In some embodiments, neither of the insert amplification primers prime or overlap with any section of the linear primer.

Figure 6:
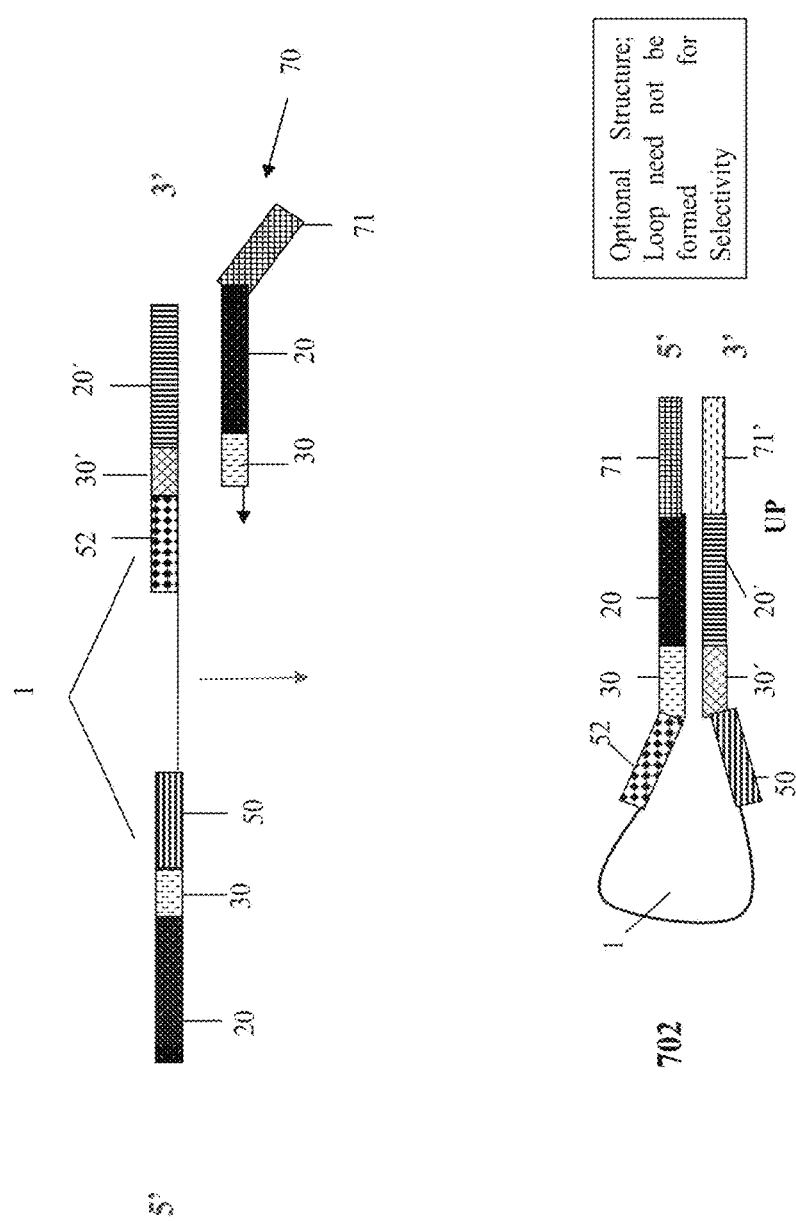
FIG. 6 depicts an embodiment of using a linear primer.

As will be appreciated by one of skill in the art, in some embodiments, it is desirable to have specific sequences on the 5' and/or 3' end of the nucleic acid sequence that have been amplified, such as the double-extended linear primer. Examples of such specific sequences include zip-code sequences, as described in U.S. Pat. Pub. No: 2006/0014191 (the entirety of which is hereby incorporated by reference). One option for achieving this is shown in FIG. 6 and FIG. 7 (which depict the self-hybridized embodiments only, although one of skill in the art can adjust the figures for the non-self-hybridized embodiments as well). In such embodiments, rather than (or following) the amplification step depicted in FIG. 3 involving the amplification primer 60, one performs an amplification step to add a desired sequence (e.g., 71) to one end of the double-extended linear primer via a different primer 70. This process, and the resulting product, 702 are shown in FIG. 6 for a double-extended linear primer that has a significant amount of target nucleic acid sequence in it, and in FIG. 7, for a double-extended linear primer that has an insignificant amount of target DNA in it.

In some embodiments, there is a first amplification primer 70 which, while including the universal priming region 20 (and optionally the noncomplementary region), includes an additional section 71. This section 71 allows one to customize the end(s) of the double-extended linear primer. As will be appreciated by one of skill in the art, section 71 is not a "noncomplementary" region, as defined herein, rather, it is a sequence that is not complementary to the sequence that the amplification primer 70 is hybridized to. The ability to have different sequences on each end of the nucleic acid segment can be useful in some sequencing applications. Thus, the above amplification primer 70 can be used in these situations. The primer 70 can include the noncomplementary region 30 and the universal priming region 20. As will be appreciated by one of skill in the art, different primers 70, each having a different section 71, can be added to specific double extended linear primers, allowing various double extended linear primers to be combined and processed in parallel, while still being able to identify the specific double extended linear primer. In some embodiments, two different primers or different sections can be added to each end.

As shown in the lower section of FIG. 6, when the target nucleic acid sequence 1 is included, amplification proceeds from these two primers to produce a double-extended linear primer (702). Of course, an actual looped structure need not be formed and desirable reaction kinetics can be sufficient to achieve the desired reactions.

In contrast, as shown in FIG. 7, in those situations in which very little or no target nucleic acid sequence is included between the universal priming region 20 and its complement 20', the resulting structure has a relatively smaller insert section resulting in relatively less amplification through the use of the insert amplification primers (802) (as noted above, this can be due to the faster hybridization kinetics due to the shorter linker and/or due to the smaller size of the loop structure which can physically limit processing of this area).

Specific Embodiments and Applications Useful for/in Whole Genome Amplification

In some embodiments, the above general approach is applied to an amplification technique that involves random primers, such as whole genome amplification (WGA). Presently, there are two general methods for whole genome amplification, 1) isothermal multiple displacement amplification ("MDA") and 2) thermal cycled methods, such as primer extension preamplification (PEP) or degenerate oligonucleotide primed PCR (DOP-PCR). One problem with applying these techniques to WGA is that there is a large amount of priming between the random primers, which produces excessive amounts of background random sequence. This background random sequence makes sequencing of unknown genomes difficult. Prior to the present disclosure, to get around this using MDA, one might have used constrained random primers, limiting the random primer sequence to just A or G nucleotides (excluding thymine and/or cytosine). The addition of even one such base (e.g., T), to the constrained random primer significantly degrades the resulting product. Alternatively, one could reduce the issue of primer dimer formation in MDA by constraining the reaction to very small volumes, generally less than about 60 nl, using microfluidic devices. As will be appreciated by one of skill in the art, in some applications, these approaches leave much to be desired.

The present inventors have appreciated that the linear primer technique described herein can be used as an unconstrained, random-primer-extension, PCR based approach that suppresses the background amplification of random primer sequences. Thus, in some embodiments, the random primers need not be limited to specific random regions (for example the random regions can include T and/or C), need not be limited to ultra small volumes (e.g., 60 nl or less), and/or can be used on subnanogram quantities of starting sample. In addition, the present inventors have appreciated that, in various embodiments, the random regions of the primer can be substantially shorter than previously appreciated. For example, the random regions can be less than 7, 6, or 5 nucleotides in length and as short as 4 nucleotides. In some embodiments, one or more of these advantages or aspects are present in the method. In some embodiments, one or more of these aspects can be combined in a method or a kit. In some embodiments, the kit will include a single linear primer having a degenerate 3' target specific region, but a single universal priming region. In some embodiments, the kit can further include a third and, optionally, a fourth insert amplification primer(s) for amplifying an insert section. The kit can include amplification ingredients, such as PCR ingredients. The kit can include amplification primers 60 as well. In some embodiments, the amplification primer consists or consists essentially of the universal region 20.

Figure 8:
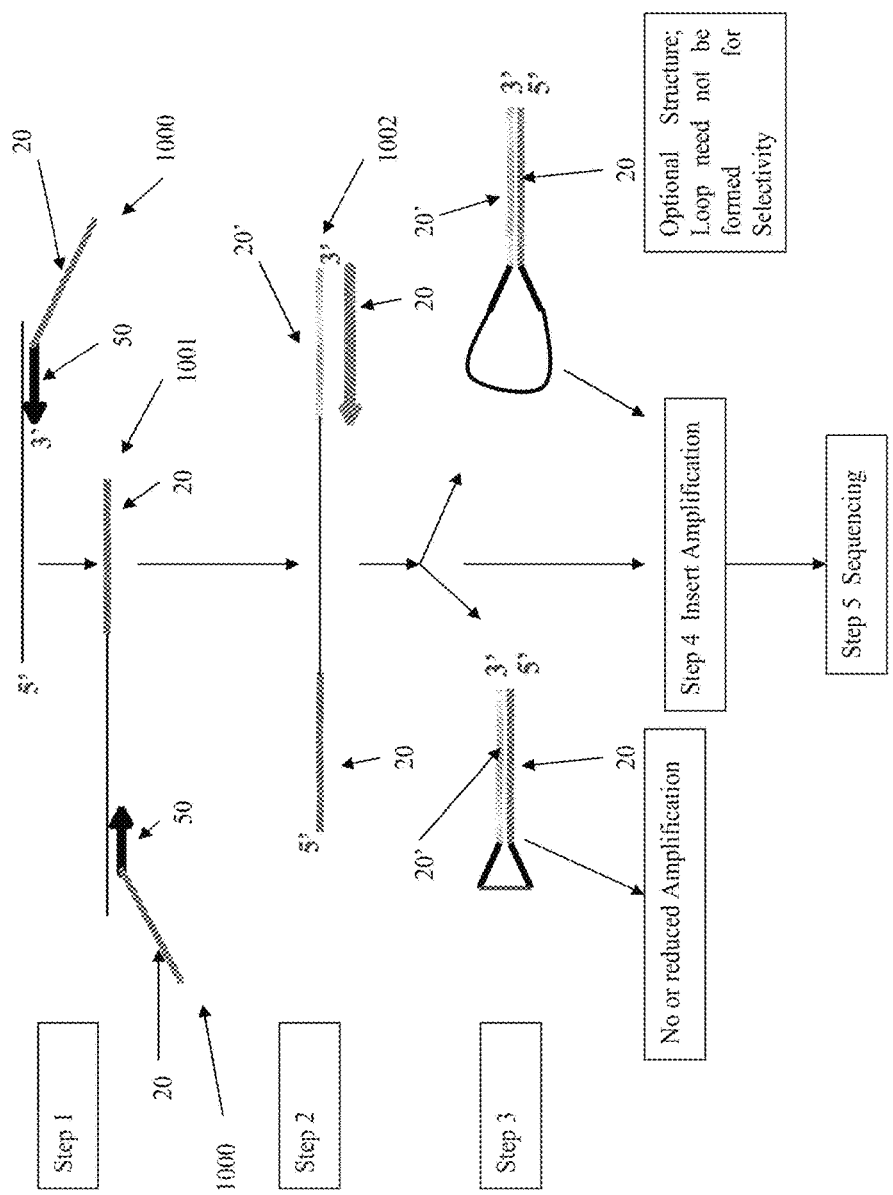
FIG. 8 depicts an embodiment of using a linear primer.

FIG. 8 generally outlines some embodiments for applying the linear primer method in a whole genome amplification application and sequencing. In the first step, the linear primer 1000 (comprising a universal priming region 20 and a random region 50) hybridizes to the target(s), via the random region 50 of the linear primer and is then extended to form the extended linear primer 1001. This in turn is hybridized to a linear primer 1000 (which can have the same sequence or at least the same universal priming region and/or noncomplementary region) and is extended to form a double-extended linear primer 1002. In some embodiments, the primer 1000 that binds to the extended linear primer has a different random region 50, as these regions can be degenerate; thus, the sequences in the random region need not, and in some embodiments is not, the same between primers 1000.

In some embodiments, the primers for this reaction can have random sequences on their 3' ends and a common, arbitrarily selected sequence (e.g., universal primer, UP, universal priming region, or universal region) on their 5'end or 5' of the 3' end.

In some embodiments, the second step comprises a single primer PCR amplification. This can be done at a higher stringency than the first step (for example, at temperatures of at least 50, 50-60, or higher than 60° C.). In some embodiments, only a primer that has the same sequence as the UP 20 in the first step is used in the second step. In some embodiments, the primer in this second step comprises (or alternatively consists essentially of or consists of) the universal priming region without the random sequences on its 3' end. In some embodiments, only a single primer sequence is used for step 2. In some embodiments, only a single primer sequence is used for step 1. In some embodiments, only a single primer sequence is used for steps 1 and 2. In some embodiments, while some of the primers in steps 1 and/or 2 may differ, all of the primers include enough sequence in common (e.g., such as the UP sequence (universal priming region) or a noncomplementary region), such that a double-extended linear primer can be formed. In some embodiments, different primers are used in step 2 or in an additional amplification step.

In some embodiments, as shown in step 3, at least part of the product from step 2 is allowed to self-hybridize (however, this is not required for all embodiments for the longer double-extended linear primers). The double-extended linear primers with short insert sections rapidly self-hybridize and remove themselves from further processing. The larger double extended linear primers are capable of amplification (step 4) for the reasons noted above. Thus, the amplification of background contaminating sequences created by the hybridization and extension of random priming sequences is curtailed because the shorter-double extended linear primer is a self-hybridizing structure that is too stable to permit efficient hybridization and extension during PCR. In some embodiments, (e.g., embodiments in which both the long and short double-extended linear primers form hairpin structures) the hairpin structures in this experiment have a calculated melting temperature in excess of 70, 75, 80, 85, or 90° C.

Following the amplification, the resulting product can be sequenced (step 5). In some embodiments, the sequencing method is a method that is suitable for whole genome analysis. In some embodiments, the sequencing method is a parallel sequencing method. In some embodiments, the sequencing method is selected from one or more of the following: supported oligo ligation detection (as disclosed in U.S. Pat. Pub. Nos. 200603845, 2008003571, and application. Ser. No. 11/345,979, incorporated by reference in their entireties), sequencing with reversible terminators (U.S. Pat. No. 6,664,079, incorporated by reference in its entirety), massive parallel sequencing, Sanger sequencing, and/or array sequencing. In some embodiments, including some embodiments in which supported oligo ligation detection is employed, an amine can be added to the 5' end of the PCR primers to reduce the ligation of the 5' end fragments of the double stranded products to the SOLiD library adaptors, thereby reducing end bias during sequencing. This can be especially useful when the initial target sequence is mRNA.

In some embodiments, the use of a linear primer as described above allows one to analyze especially low amounts of target nucleic acid in whole genome amplification. For example, in some embodiments, the initial sample contains less than 1 gram of target nucleic acid sequence, for example, 1000-100, 100-10, 10-1, 1-0.1, 0.1-0.01, 0.01-0.001, 0.001-0.0001, 0.0001-0.00001, 0.00001-0.000001 nanograms or less. In some embodiments, the amount of target nucleic acid is the amount of the target nucleic acid in a single cell. In some embodiments, the amount of target nucleic acid is between 0.5 and 100 pg. In some embodiments, the amount of target nucleic acid is less than 100 pg. As will be appreciated by one of skill in the art, this can be especially advantageous in whole genome amplification and sequencing.

In some embodiments, because the linear primers are not biased in how they initially bind to the target nucleic acid sequence (e.g., in contrast to looped primers), they can bind along and within stretches of DNA, thereby avoiding having to over process the gDNA to make relatively short pieces of gDNA for amplification. In some embodiments, the method avoids overprocessing the initial sample. In some embodiments, the methods avoid sonication, avoid blunt end steps, and/or avoid anchors. As will be appreciated by one of skill in the art, this can be especially advantageous in whole genome amplification and sequencing.

In some embodiments, by using the herein presented techniques, one can avoid a precleaning step, such as fragment size selection. Thus, in some embodiments, the method does not include a precleaning step, such as fragment size selection. As will be appreciated by one of skill in the art, this can be especially advantageous in whole genome amplification and sequencing.

In some embodiments, any of the methods can be applied in or for a clinical and/or forensics environment. In some embodiments, the technique is applied in molecular oncology. In some embodiments, the technique is applied to a sample in which the actual tumor cell content in the sample is less than 70%, e.g., 70-65, 65-60, 60-10, 10-1, 1-0.1, 0.1-$10^{-2}$, $10^{-2}$-$10^{-3}$, $10^{-3}$-$10^{-4}$, $10^{-4}$-$10^{-5}$, $10^{-5}$-$10^{-6}$, $10^{-6}$-$10^{-7}$% or less of the sample. As will be appreciated by one of skill in the art, this can be especially advantageous for whole genome amplification and sequencing. In some embodiments, this can be used in laser captured single cells.

In some embodiments, the relatively large increases in amplification are achieved while still maintaining a significant amount of dose response during the amplification. For example, in some embodiments, relatively small amounts of one species to be amplified will still be a relatively small percent of the amplified product (although it could have been amplified, e.g., 100-1,000,000 times). As will be appreciated by one of skill in the art, this can be especially advantageous in whole genome amplification and sequencing.

As will be appreciated by one of skill in the art, while the single primer amplification embodiment ameliorates the problem of random background sequence amplification, it can introduce kinetic parameters that impact the levels of amplification. During the formation of the double extended linear primer, with every thermal cycle a significant amount of primer is expected to be removed by primer-primer hybridization and extension. As such, in some embodiments, it can be advantageous to use relatively high levels of primer. In some embodiments, 10 microM or more can be used, for example, 10-100, 100-1000, 1000-10,000, 10,000-100,000 microM can be used. In some embodiments new primer can be added during or throughout the procedure.

Embodiments Having a Relatively Short 3' Target Specific Region

In some embodiments, the linear primer comprises, consists, or consists essentially of a relatively short 3' target specific regions, such as a short 3' random region. In some embodiments, this shorter 3' target specific region is used in whole genome amplification where one starts with a low amount of DNA. In some embodiments, the 3' target specific region is less than 15 nucleotides in length, for example, 15, 14, 13, 12, 11, 10, 9, 8, 7, 6, 5, 4, or 3 nucleotides. In some embodiments, the 3' target specific region is between 9 and 2, 8 and 3, 7 and 3, 6 and 3, or 6 and 4 nucleotides in length. As will be appreciated by one of skill in the art, the shorter length of the random sequence allows for more frequent binding of the primer to the target DNA, which can be especially advantageous in whole genome amplification and sequencing. In some embodiments, the number of degenerate or random nucleotides is between 5 and 12, 5 and 13, 5 and 14, or 5 and 15.

Random Region Sequences that are not Constrained to A and/or G

In some embodiments, the linear primer (and its methods of use) allows one to use a 3' target specific region that is not constrained to just A or G in whole genome amplification. In some embodiments, the 3' target specific region is or includes a random and/or degenerate region. In some embodiments, this region includes T and/or C in the random region. As will be appreciated by one of skill in the art, this does not mean that the region is no longer "random."

In some embodiments, the random region includes at least one thymine. In some embodiments, the random region includes at least one cytosine. In some embodiments, at least one of the primers in the amplification reaction includes a cytosine and/or thymine in the random region. In some embodiments, at least one of the primers in the amplification reaction includes, in the random region, at least one nucleotide that is not an adenine or a guanine. In some embodiments, the base or nucleotide is or comprises a thymine, cytosine, or uracil, nucleotide analog (e.g., including thymine, uracil, and/or cytosine analogs), or other option. In some embodiments, the random region includes at least 2, 3, 4, 5, 6, 7, 8, 9, 10, 11, 12, or more nucleotides that are cytosine and/or thymine. In some embodiments, the random region includes at least 2, 3, 4, 5, 6, 7, 8, 9, 10, 11, 12, or more nucleotides that are not adenine and/or guanine. As will be appreciated by one of skill in the art, removing this constraint can be especially advantageous in WGA applications and sequencing.

Embodiments Involving Unconstrained Volumes

In some embodiments, the use of a linear primer allows one to analyze samples that are relatively large in volume compared to standard whole genome amplification techniques (such as the MDA techniques described herein). For example, in some embodiments, the sample is more than 60 nl, for example, 60-80, 80-100, 100-200, 200-500, 500-1000, 1000-10,000, 10,000-100,000, 100,000-1,000,000 nl or more in volume. In some embodiments, an initial sample is diluted or brought up to a volume that is above 60 nl, for example, 60-80, 80-100, 100-200, 200-500, 500-1000, 1000-10,000, 10,000-100,000, 100,000-1,000,000 nl or more. In some embodiments, a sample to be analyzed starts off as a dry or non-liquid sample and a volume of liquid is added to the sample to suspend the sample. In some embodiments, the volume used to suspend the sample is more than 60 nl, for example, 60-80, 80-100, 100-200, 200-500, 500-1000, 1000-10,000, 10,000-100,000, 100,000-1,000,000 nl or more. In some embodiments, any one or more of the steps outlined in FIG. 8 (steps 1-5) is carried out in a volume that is above 60 nl, for example, 60-80, 80-100, 100-200, 200-500, 500-1000, 1000-10,000, 10,000-100,000, 100,000-1,000,000 nl or more. In some embodiments, at least one of the amplification steps in FIG. 8 is carried out in a volume that is above 60 nl, for example, 60-80, 80-100, 100-200, 200-500, 500-1000, 1000-10,000, 10,000-100,000, 100,000-1,000,000 nl or more. As will be appreciated by one of skill in the art, removing the volume constraint can be especially advantageous in WGA applications and sequencing.

As will be appreciated by one of skill in the art, the above embodiments can be achieved via the use of a linear primer that results in the formation of a double extended linear primer that can self-hybridize (at least for the shorter double-extended linear primers). Thus, in some embodiments, each piece of amplified DNA will have two sections that can hybridize to each other. In some embodiments, this is achieved via the use of a single linear primer in the amplification reaction (such that the amplified DNA has a sequence that is the linear primer on one end and the complement of the linear primer on the opposite end). In some embodiments, this can be achieved via the use of different primers, where all of the primers share a common sequence (such as the universal priming region, a random region, and/or a noncomplementary region) such that they can still produce the double extended linear primer that can self-hybridize.

Additional Embodiments

In some situations, after incorporation of a universal priming region, universal primers will still have a problem of having some homology with internal sequences in highly complex populations of long gDNA fragments from the whole genome. Where the concentration of the universal primers are typically on a µM scale, even partial matches of the 3' end of the universal primers with internal sequences of gDNA fragments can generate shorter products. These shorter products can be preferentially amplified by high concentrations of universal primers. Thus, some of the present embodiments can be used to limit the generation of these short products from primer-dimers or spurious internal priming. In some embodiments long tracts of dT bases can be used in the linear primer (as a noncomplementary region for example) for the above reason and because the frequency of poly dT in the middle of gDNAs can be low. In other embodiments, tracts of sequences rarely found in the target genome are used as a noncomplementary region.

As will be appreciate by one of skill in the art, while the 3' target specific region often includes a random or degenerate region, in some embodiments, the sequence is a specific sequence or collection of specific sequences. In some embodiments, the linear primer can include additional sequence sections to those described above. In other embodiments, the linear primer only includes those sections depicted in FIG. 1A. Additionally, as will be appreciated by one of skill in the art, some of the presently disclosed techniques can be applied to RNA amplification as well, for example, by including an initial reverse transcription step.

As will be appreciated by one of skill in the art, in some embodiments, a noncomplementary region is used throughout numerous primers, allowing for multiple primers, such as primers including universal, random, or degenerate regions, to be used with a reduced risk of undesired priming events. This can be useful in multiplexed reactions in which numerous different starting primers are employed.

In some embodiments, the above methods can allow for a significant amount of amplification to occur. In some embodiments, the amplification is of nucleic acid sequences of a significant length (e.g., 200 or more nucleic acids). In some embodiments, the amplification of these lengths of target nucleic acid sequences, across a genome's worth of nucleic acid sequence, is achieved. In some embodiments, at least a fraction of the genome is amplified, e.g., 0-1, 1-5, 5-10, 10-20, 20-30, 30-40, 40-50, 50-60, 60-70, 70-80, 80-90, 90-95, 95-99, or 99-100% of the genome is amplified. In some embodiments, at least some fraction of the fraction amplified is of the desired length, e.g., 0-1, 1-5, 5-10, 10-20, 20-30, 30-40, 40-50, 50-60, 60-70, 70-80, 80-90, 90-95, 95-99, or 99-100% is at least 200 bp in length.

In some embodiments, the amount of amplification across a genome is substantially similar. In some embodiments, the amount of amplification for the various target nucleic acids sequences is the same. In other words, sequences A-Z are all amplified to a similar extent so that the resulting ratio of product nucleic acid sequences is the substantially the same for sequences A-Z. In some embodiments, the ratios are maintained in a qualitative manner (e.g., there is more of sequence A than sequence B).

In some embodiments, the amount of amplification of the desired fragments that is achieved is substantial. For example, amplification of the initial product over 30 fold can be achieved, e.g., 30-100, 100-1000, 1,000-3000, 3000-10,000, 10,000-50,000, 50,000-100,000, 100,000-500,000, 500,000-800,000, 800,000-1,000,000, 1,000,000-10,000,000 fold or more. In some embodiments this is achieved with a reduced amount of primer dimer formation and/or spurious priming. In some embodiments, the amount of primer dimers is reduced by at least some amount, e.g., 0-1, 1-5, 5-10, 10-20, 20-30, 30-40, 40-50, 50-60, 60-70, 70-80, 80-90, 90-95, 95-99, or 99-100%.

As noted above, some of the embodiments can be advantageously used when random and/or degenerate priming regions are employed at the 3' target specific region of the primer, when universal primers are used, or when both aspects are used. Moreover, in some embodiments, further benefits can be obtained when numerous such primers (or other non-linear primers) are combined within a reaction (such as in multiplexed or subsequent amplification or extension reactions). As such, as noted above, some of the embodiments can be useful for whole genome amplification. However, not all of the disclosed embodiments are limited to such applications. Even amplification reactions that do not include random regions, or do not involve whole genome amplification can benefit from some of the above embodiments. For example, some of the above embodiments will reduce the number or amount of relatively short nucleic acid sequences that are amplified from a target. As will be appreciated by one of skill in the art, these shorter sequences can be problematic for a variety of reasons (e.g., since they are shorter, they will dominate subsequent amplification reactions). Additionally, the insertion of the noncomplementary region generally allows for one to use either a random, specific, or mix thereof, region for target hybridization, while reducing the likelihood that the target sequence will hybridize too frequently or nonspecifically.

In some embodiments, the linear primers and relevant methods are employed in massively multiplexed procedures in which various linear primers are employed. As will be appreciated by one of skill in the art, the above embodiments employing degenerate ends at the 3' target specific region of the probe is one form of multiplexing. However, in some embodiments, different sequences are also employed within the linear primer so as to provide a degree of separation or distinctness among the amplified products. In some embodiments, these different sequences are in the universal priming section, a tag sequence, or other additional section added to the linear primer. In some embodiments, the number of primers having these different sequences (apart from differences in the 3' target specific region) are at least 2, if not more, for example, 2-5, 5-10, 10-20, 20-30, 30-50, 50-100, 100-200, or more primers can be used. In some embodiments, the primers can include specific bar-code sequences to allow for ease of identification.

In some embodiments, the linear primer and various embodiments disclosed herein are used for assisting in forensic analysis. In some embodiments, the linear primer and various embodiments disclosed herein are employed in amplifying a target nucleic acid sequence for DNA fingerprinting. In some embodiments, the linear primer and various embodiments disclosed herein are employed in amplifying short tandem repeats ("STR") from a sample that is to be identified or matched to another sample. In some embodiments, the linear primer includes a sequence that can be used to amplify a STR locus. In some embodiments, the insert amplification primer includes a sequence that can be used to amplify a STR locus.

In some embodiments, the double-extended linear primer is created as described by any of the embodiments described herein. Once the double extended linear primer is created, and optionally amplified by an amplification primer, one or more insert amplification primers can be used to amplify the insert section. In some embodiments, the insert amplification primers will hybridize to sections upstream or downstream of one or more STR loci to be amplified. In some embodiments, the insert amplification primer comprises or consists of a STR primer. Thus, in some embodiments, the double-extended linear primer can be used for efficient amplification of a target or target genome and the use of STR-primers (or insert amplification primers that can be used to amplify a STR locus) can be used to further selectively amplify and/or detect the presence of specific STRs in a sample. In some embodiments, the insert amplification primer is a STR-primer that can amplify the locus of one or more of the 13 standard STRs examined for DNA fingerprinting. In some embodiments, the insert amplification primer is a STR-primer that can amplify the locus of one or more of the currently 13 standard STRs examined for DNA fingerprinting.

In some embodiments, rather than using a STR specific aspect towards the end of the process, the linear primer itself comprises an aspect that will direct it to the amplification of STRs or sequences around STRs. For example, in some embodiments, the 3' target specific region, rather than being a random or degenerate region, comprises or consists of a STR-primer sequence that can be used to amplify a STR locus. Apart from this modification, the remaining steps can include any of those disclosed herein. In such an embodiment, the insert amplification primers do not need to be STR primers (although they can be).

A "STR-3' target specific region" denotes a 3'target specific region that will serve as a STR-primer (and thus can be used to amplify a STR locus).

A "STR-primer" is a primer that can be used to amplify a STR locus.

In some embodiments, the locus is one or more of TH01, TPOX, CSF1PO, vWA, FGA, D3S1358, D5S818, D7S820, D13S317, D16S539, D8S1179, D18S51, D21S11, D2S1338, D3S1539, D4S2368, D9S930, D10S1239, D14S118, D14S548, D14S562, D16S490, D16S753, D17S1298, D17S1299, D19S253, D19S433, D20S481, D22S683, HUMCSF1PO, HUMTPOX, HUMTH01, HUMF13AO1, HUMBFXIII, HUMLIPOL, HUMvWFA31, Amelogenin, D12s391, D6S1043, SE33, or any combination thereof. In some embodiments, the locus is one or more of CSF1PO, FGA, TH01, TPOX, vWA, D3S1358, D5S818, D7S820, D8S1179, D13S317, D16S539, D18S51, D21S11, D19S433, and D2S1338. In some embodiments, the locus is a "CODIS loci" or "CODIS locus." This refers to the STR loci designated by the FBI's "Combined DNA Index System." Thirteen core STR loci are TH01, TPOX, CSF1PO, vWA, FGA, D3S1358, D5S818, D7S820, D13S317, D16S539, D8S1179, D18S51, and D21S11. (See, e.g., Butler, Forensic DNA Typing, Academic Press (2001), at page 63.)

In some embodiments, more than one locus is amplified in one reaction. In some embodiments, two, three, four, five, six, seven, eight, nine, ten, eleven, twelve, thirteen, fourteen, fifteen, sixteen, seventeen, eighteen, nineteen, twenty or more loci are co-amplified. In some embodiments employing multiplex co-amplification, not all of the primer pairs comprise a high stability primer.

After amplification, the products from the PCR reactions can be analyzed, resolved, and/or characterized by any of a variety of methods known in the art. For example, PCR reactions can be analyzed by denaturing samples and separating using gel electrophoresis or a capillary electrophoresis protocol. The results from this can then allow one to determine the number of repeats of the STR sequence that are present.

Aspects of the present teachings may be further understood in light of the following examples, which should not be construed as limiting the scope of the present teachings in any way.

EXAMPLE 1

Amplification of gDNA

This example describes how one can employ linear primers for the amplification of a substantial portion of a genome.

First, one obtains, provides, or is provided a sample that includes genomic DNA. The genomic DNA in the sample is isolated from various non-DNA impurities in the sample, if necessary. Following this, a linear primer is added to the solution containing the gDNA. The linear primer can include a degenerate section and therefore actually comprise numerous primers, each having a different 3' target specific sequence. The linear primer is then extended to eventually form a double-extended linear primer.

Following this, an amplification step can be performed with one or more amplification primers. Each amplification primer includes a section that is substantially identical in sequence to the universal priming region and the non-complementary region in the original linear primer. PCR can then be performed on the solution, using this amplification primer.

Following this, a digest is optionally performed on the solution so that any single stranded primers are eliminated. This can be achieved via exonuclease I.

Following this, the conditions of the solution are adjusted, if necessary, to allow the shorter amplified double-extended linear primer to self-hybridize.

Insert amplification primers are then added to the solution. The insert amplification primers can be degenerate primers or universal primers.

The amplified double-extended linear primer can also be divided into separate containers (such as wells) and a specific insert amplification primer (or primer set) added to each container to allow amplification to occur based on that specific insert amplification primer (or set). Numerous such insert amplification primers can be used in series or parallel in the separate containers. A PCR is performed on the solution (or more specifically for each solution) under conditions that allow the annealing and extension of the insert amplification primers.

The above steps will result in the amplification of the target nucleic acid sequence.

EXAMPLE 2

General Amplification Process

The present example generally describes the parameters used for the other examples presented herein. As will be appreciated by one of skill in the art, these are just exemplary parameters and are not limiting on various embodiments.

The reaction for step 1 (extension/pre-PCR, as shown in FIG. 8) was done in 20 µl containing: 2 µl 10×PCR Buffer II (Applied Biosystems); 10 µM UP primer with random sequence on the 3' end (5'TCATGATCCGTGGAGTCG-GCTTTTTTTTTTN$_n$3', SEQ ID NO: 1 where N is one or more of A, C, T, or G) purchased from IDT); 4 µl Ampli- Taq®, 5 U/µl; 5 mM NTP; 3 mM Mg Cl$_2$; 4 µl of DNA to be amplified. The reaction mix was heated to 95° C. for 1 minute and then given 20 cycles of the following temperature pattern: 95° C. for 15 seconds, 16° C. for 2 minutes, 35° C. for 2 minutes, 65° C. for 2 minutes. The reaction for step 2 (pre-PCR with single primer, FIG. 8) was done in 40 µl containing: 20 µl of the mixture from step 1; 4 µl 10×PCR Buffer II (Applied Biosystems); 10 µM UP primer (5'TCATGATCCGTGGAGTCGGCTTTTTTTTTT3', SEQ ID NO: 2) purchased from IDT); 4 µl AmpliTaq®, 5 U/µl; 2.5 mM NTP; 1.5 mM MgCl$_2$. The reaction mix of step 2 was heated to 95° C. for 1 minute and then given 10-25 cycles of the following temperature pattern: 95° C. for 15 seconds, 65° C. for 2 minutes, 72° C. for 2 minutes. Finally, residual primers were removed from the resultant mixture by treatment with Exonuclease 1. To do this for individual gene analysis for example, 10 µl of mixture was combined with 4 µl ExoZAP-IT (USB) and incubated at 37° C. for 15 minutes; exonuclease was inactivated by heating at 85° C. for 5 minutes. The sample was then diluted with distilled water to 200 microliters. For this work, all reactions were done on a clean bench surface using prepackaged disposable pipette tips and tubes.

The above conditions were used for the relative amplification of various selected genes by real time PCR. The 10 µl TaqMan® reactions contained: 2 µl of exonuclease treated amplified DNA, 5 µl 2× Universal Master Mix Applied Biosystems, 1 µl 10×AB TaqMan® FAM gene dosage assay stock, 1 µl 10×AB TaqMan® VIC RNase P reference assay stock, 1 µl H$_2$O.

EXAMPLE 3A

Efficiency of Random Priming

The present example tested the relative efficiency of random priming as a function of random primer length.

Figure 9:
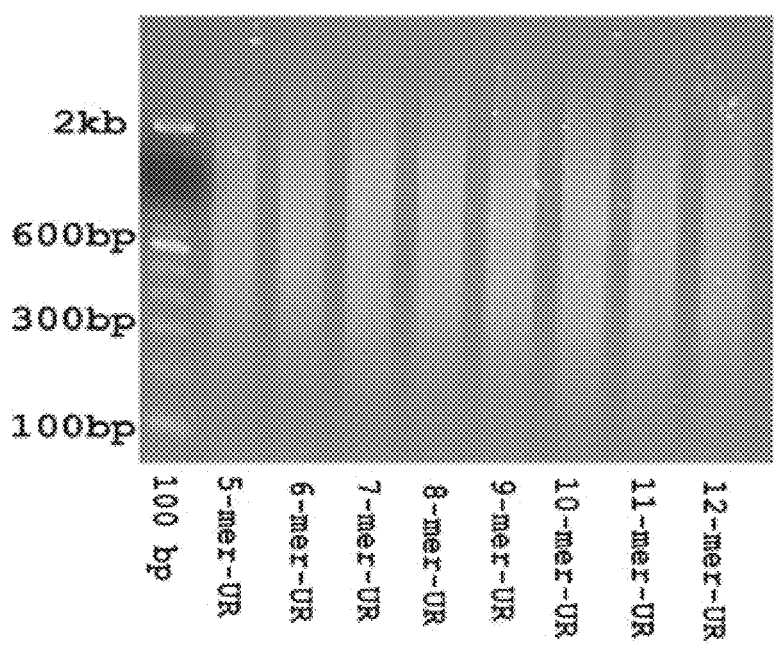
FIG. 9 is a representation of a gel demonstrating the ability of various lengths of random regions in a linear primer to work in various embodiments to amplify a nucleic acid.

To determine the relative efficiency of random priming in relation to random primer length, 3' random primer lengths of 5 to 12 nucleotides were used in the linear primer and used to amplify 4 ng of human DNA. The results are presented in FIG. 9, which depicts an electrophoretic gel that compares the amplification of 4 ng CEPH human DNA with random priming lengths of 5 to 12 nucleotides. Amplified DNA using these different primer lengths resulted in SYBR green monitored Ct values for RNase P of 27.52, 26.53, 24.98, 22.83, 22.48, 21.02, 22.78, and 23.81, respectively.

Interestingly, all random primer lengths examined amplify the genome, with random sequences as short as 5 nucleotides priming with surprising efficiency. The size of the amplified sequences centers around about 1000 nucleotide pairs in length with the range varying from about 100 to several thousand nucleotides. Thus, it is apparent that, for the present embodiments, random regions that are 7, 6, or 5 nucleotides in length work adequately.

In addition, given the quality of the results for the 5 nucleotide experiment, it is likely that shorter random primer lengths will work as well, e.g., 4, nucleotides in length.

EXAMPLE 3B

The present example demonstrates that the single primer amplification worked to curtail random primer interactions. A collection of primers were subjected to real time 50 cycle analysis at 60° C. incubation in the presence of SYBR green to follow product amplification. No product was observed after 50 cycles of real-time PCR, even for primers that contained 12 nucleotides of random sequence on the end.

As will be appreciated by one of skill in the art, under these conditions, typical two primer PCR would have generated severe primer-dimer amplification. As such, it appears that some of the various embodiments are effective at preventing primer dimerization.

EXAMPLE 4

Titration of DNA

Figure 10:
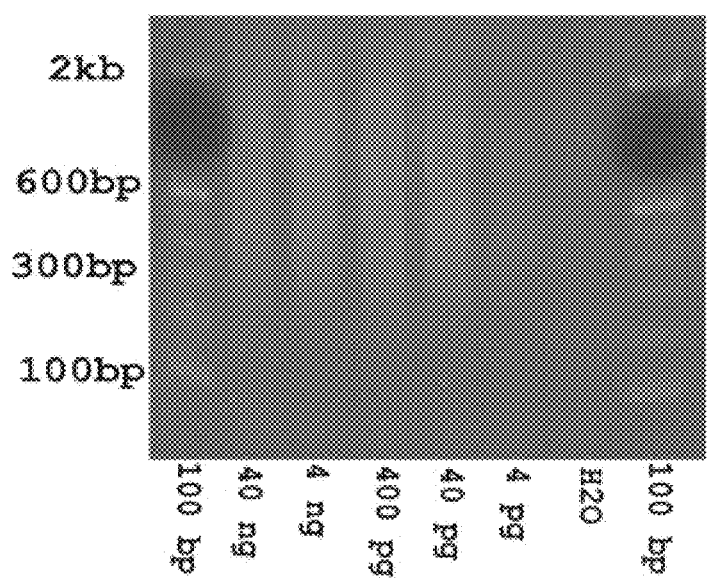
FIG. 10 is a representation of a gel demonstrating the results of amplification from various concentrations of starting material.

FIG. 10 shows the results of a titration of input DNA for primers with random sequences of 8 nucleotides on their 3' end, and 20 cycles of amplification in step 2. The amplification appears to reach similar levels down to DNA input levels as low as 40 pg or about 6 diploid cells and then drops off at an input DNA level of 4 pg or 0.6 of a diploid cell. Real time PCR for the reference gene, RNase P, indicated that the genomic amplification is saturated down to the 40 pg input level and that the reference gene is not present in whatever is amplified below this level (Table 4.1)

TABLE 4.1

|  | 1x | SD | 10x | SD | 12x | SD | 15x | SD | 18x | SD | 20x | SD | Control | SD | Amplification folds for 20x | Step#2 for 20x | Step#1 for 20x |
|---|---|---|---|---|---|---|---|---|---|---|---|---|---|---|---|---|---|
| Taq-FAM (RNaseP) | | | | | | | | | | | | | | | | | |
| CEPH 40 ng | 30.19 | 0.11 | 24.21 | 0.11 | 23.50 | 0.20 | 22.56 | 0.09 | 22.25 | 0.11 | 22.16 | 0.09 | 24.43 | 0.19 | 960 | 260 | 4 |
| CEPH 4 ng | 33.20 | 0.10 | 26.40 | 0.07 | 24.01 | 0.12 | 22.35 | 0.10 | 22.07 | 0.02 | 21.70 | 0.21 | 27.59 | 0.10 | 11880 | 2893 | 4 |
| CEPH 400 pg | 37.33 | 1.85 | 28.55 | 0.22 | 27.64 | 0.36 | 24.31 | 0.18 | 22.84 | 0.02 | 21.90 | 0.19 | 30.95 | 0.02 | 106319 | 44241 | 2 |
| CEPH 40 pg | 40.00 | 0.00 | 31.57 | 0.12 | 28.25 | 0.20 | 28.03 | 0.10 | 23.24 | 0.14 | 22.77 | 0.03 | 34.35 | 0.18 | 610094 | 153650 | 4 |
| CEPH 4 pg | 40.00 | 0.00 | 40.00 | 0.00 | 40.00 | 0.00 | 40.00 | 0.00 | 40.00 | 0.00 | 40.00 | 0.00 | 38.91 | 1.54 | 94 | 1 | 94 |
| NTC | 40.00 | 0.00 | 40.00 | 0.00 | 40.00 | 0.00 | 40.00 | 0.00 | 40.00 | 0.00 | 40.00 | 0.00 | 40.00 | 0.00 | 200 | 1 | 200 |
| SYBR (Rnase P) | | | | | | | | | | | | | | | | | |
| CEPH 40 ng | 26.52 | 0.05 | 20.79 | 0.12 | 20.49 | 0.03 | 19.50 | 0.29 | 19.61 | 0.10 | 18.94 | 0.63 | 20.69 | 0.08 | 672 | 192 | 4 |
| CEPH 4 ng | 29.72 | 0.14 | 22.98 | 0.11 | 20.71 | 0.11 | 19.57 | 0.08 | 18.76 | 0.25 | 18.94 | 0.22 | 23.59 | 0.52 | 5021 | 1761 | 3 |
| CEPH 400 pg | 31.48 | 0.42 | 24.94 | 0.22 | 24.10 | 0.13 | 21.09 | 0.02 | 19.65 | 0.05 | 18.77 | 0.05 | 26.68 | 0.48 | 48089 | 6695 | 7 |
| CEPH 40 pg | 34.24 | 0.24 | 27.88 | 0.20 | 24.51 | 0.06 | 24.45 | 0.11 | 19.81 | 0.08 | 19.76 | 0.05 | 31.09 | 0.82 | 512909 | 22788 | 23 |
| CEPH 4 pg | 36.47 | 0.40 | 34.39 | 0.86 | 34.84 | 0.66 | 29.04 | 0.75 | 31.71 | 0.61 | 32.12 | 0.33 | 34.66 | 0.93 | 1161 | 20 | 57 |
| NTC | 35.76 | 1.71 | 40.00 | 0.00 | 38.93 | 1.51 | 32.57 | 0.70 | 36.46 | 0.63 | 32.32 | 1.00 | 40.00 | 0.00 | 41119 | 11 | 3778 |

The results in Table 4.1 were from the amplification of RNase P (via a single primer), monitored by real time PCR using both SYBR green and RNase P specific TaqMan® probe. Table 4.1 indicates that the plateau in amplification appears when the Ct for RNase P is about 19 for SYBR green measurements, and 22 as measured by a TaqMan® RNase P specific probe. Nanogram levels of input DNA appeared to plateau by 15 cycles, while 400 pg of DNA plateaus by 18 cycles, and 40 pg around 20 cycles. The last three columns of Table 4.1 estimate the actual amount of amplification that has occurred when compared to unamplified, undiluted control DNA, and partition the amount of amplification between step 1 and step 2. The dilutions involved in the amplification procedure are part of the calculation of the amplification level.

The estimates for the amount of amplification differ for SYBR green and TaqMan® The TaqMan® method is more dependable because SYBR green Cts measure all double stranded DNA and after many rounds of amplification substantial unspecific amplification can suppress the real time Ct estimates for amplified DNA. Table 4.1 clearly shows that the bulk of the amplification occurs in step 2.

EXAMPLE 5

Various Genes

Figure 11A:
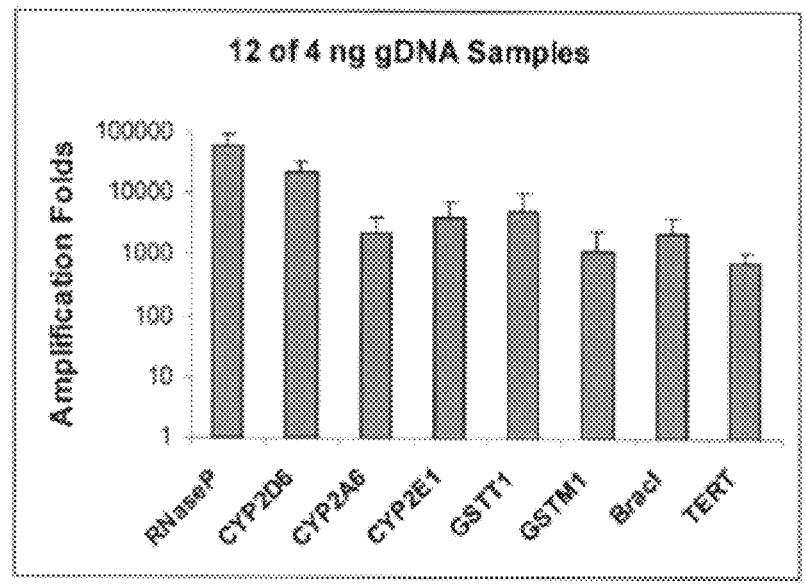
FIG. 11A is a table demonstrating the ability of some of the embodiments to amplify gDNA.
Figure 11B:
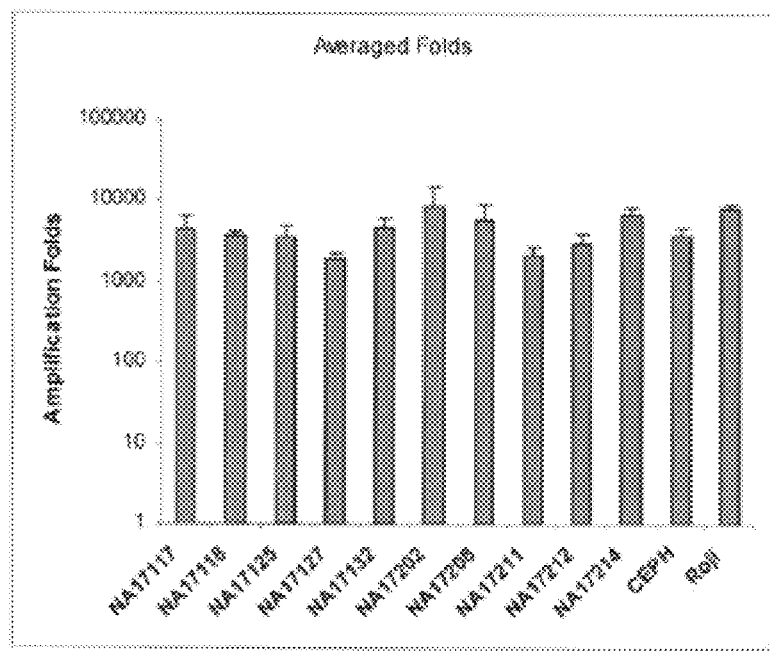
FIG. 11B is a table demonstrating the ability of some of the embodiments to amplify gDNA.

To verify the wide applicability of the protocol, the amplification yields of 12 different DNAs were evaluated for 8 different genes (using the method outlined above). The amplification folds for the different human gDNAs were within 2 folds for each of all 8 genes in the different gDNAs. FIG. 11A shows the average amplification levels of 8 genes for 12 different human DNA types; the largest difference of amplification between the genes is 80 fold. FIG. 11B shows the relative averaged amplification of all 12 monitored genes for 4 ng of the 12 different human DNA of this study.

EXAMPLE 6

Comparison of Linear Primers and Loopable Primers

Figure 12A:
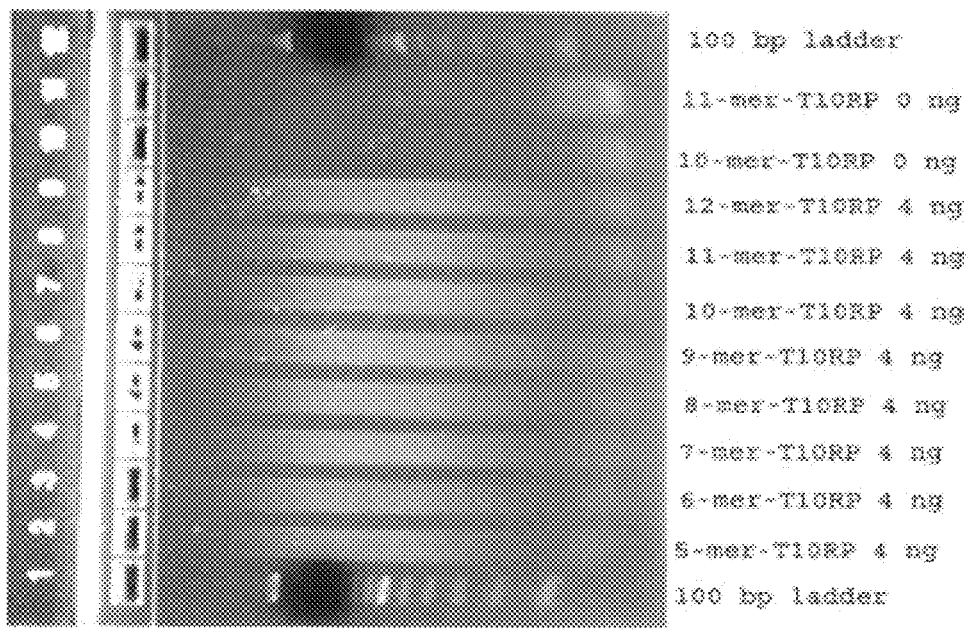
FIG. 12A is a representation of a gel demonstrating the results of amplification from various lengths of random regions in a linear primer.
Figure 12B:
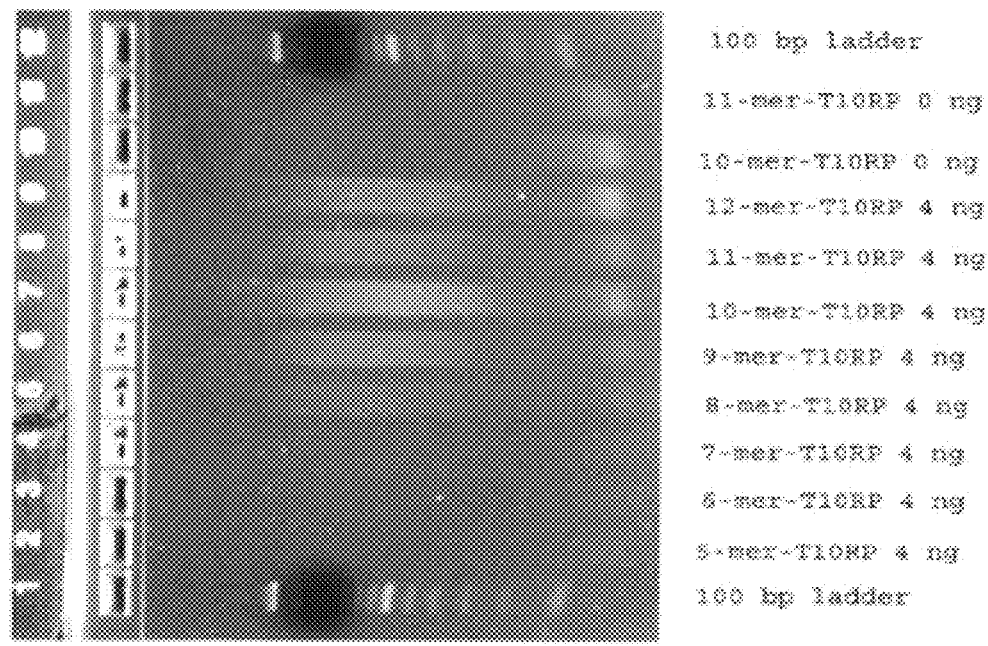
FIG. 12B is a representation of a gel demonstrating the results of amplification from various lengths of random regions in a looped primer.

Linear and stem-loop primers with different lengths of 3' random sequences were used to amplify 4 ng of DNA. The results are presented in FIGS. 12A and 12B. As can be observed in the gels, the stem-loop structure virtually eliminates efficient internal priming until a random 3' sequence length of about 10 nucleotides. In contrast, the same 3' region on the linear primer appears to yield sufficient amounts of product, even for 3' target regions that are 5 oligonucleotides. The Ct results for the random base numbers are presented in Table 6.1 below.

TABLE 6.1

| CEPH 4 ng | Linear N5 | SD | Linear N6 | SD | Linear N7 | SD | Linear N8 | SD |
|---|---|---|---|---|---|---|---|---|
| CYPZO5 | 27.73 | 0.30 | 25.83 | 0.20 | 22.19 | 0.31 | 25.43 | 0.02 |
| CYPZA5 | 36.53 | 1.54 | 28.15 | 0.05 | 24.51 | 0.02 | 24.08 | 0.09 |
| CYP2E1 | 22.75 | 0.12 | 21.39 | 0.08 | 23.92 | 0.09 | 23.75 | 0.27 |
| GSTT1 | 29.15 | 0.08 | 27.64 | 0.01 | 24.76 | 0.05 | 25.18 | 0.03 |
| GSTM1 | 38.70 | 1.83 | 29.43 | 0.51 | 33.83 | 0.62 | 40.00 | 0.00 |
| RNaseP | 23.04 | 0.06 | 22.63 | 0.05 | 21.67 | 0.16 | 21.38 | 0.22 |
| CEPH 0 ng | Linear N5 | SD | Linear N6 | SD | Linear N7 | SD | Linear N8 | SD |
| CYP2D8 | 40.00 | 0.00 | 40.00 | 0.00 | 40.00 | 0.00 | 40.00 | 0.00 |
| CYP2A6 | 40.00 | 0.00 | 40.00 | 0.00 | 40.00 | 0.00 | 40.00 | 0.00 |
| CYP2E1 | 40.00 | 0.00 | 40.00 | 0.00 | 40.00 | 0.00 | 40.00 | 0.00 |
| GSTT1 | 40.00 | 0.00 | 40.00 | 0.00 | 40.00 | 0.00 | 40.00 | 0.00 |
| GSTM1 | 40.00 | 0.00 | 40.00 | 0.00 | 40.00 | 0.00 | 40.00 | 0.00 |
| RnaseP | 35.52 | 0.50 | 34.80 | 0.35 | 35.79 | 0.55 | 35.64 | 0.46 |
| CEPH 4 ng | Loop N5 | SD | Loop N6 | SD | Loop N7 | SD | Loop N8 | SD |
| CYP2D6 | 35.32 | 0.71 | 35.31 | 0.37 | 33.93 | 0.62 | 23.99 | 0.10 |
| CYP2A6 | 35.70 | 0.23 | 37.92 | 2.24 | 36.57 | 0.94 | 22.62 | 0.18 |
| CYP2E1 | 37.36 | 3.73 | 34.69 | 0.02 | 34.44 | 0.14 | 26.62 | 0.01 |
| GSTT1 | 35.46 | 0.16 | 36.05 | 0.55 | 34.52 | 0.74 | 25.69 | 0.40 |
| GSTM1 | 38.78 | 1.72 | 38.08 | 2.72 | 40.00 | 0.00 | 38.07 | 2.73 |
| RNaseP | 38.04 | 0.04 | 36.63 | 0.89 | 35.73 | 0.43 | 22.87 | 0.07 |
| CEPH 4 ng | Loop N5 | Loop N5 | Loop N6 | Loop N6 | Loop N7 | Loop N7 | Loop N8 | Loop N8 |
| CYP2D6 | 40.00 | 0.00 | 40.00 | 0.00 | 40.00 | 0.00 | 40.00 | 0.00 |
| CYP2A6 | 40.00 | 0.00 | 40.00 | 0.00 | 40.00 | 0.00 | 40.00 | 0.00 |
| CYP2E1 | 40.00 | 0.00 | 38.53 | 1.72 | 40.00 | 0.00 | 40.00 | 0.00 |
| GSTT1 | 36.47 | 4.99 | 39.33 | 0.94 | 40.00 | 0.00 | 40.00 | 0.00 |
| GSTM1 | 40.00 | 0.00 | 40.00 | 0.00 | 40.00 | 0.00 | 40.00 | 0.00 |
| RNaseP | 37.88 | 1.16 | 40.00 | 0.00 | 39.27 | 1.03 | 37.68 | 1.10 |
| | Linear N9 | SD | Linear N10 | SD | Linear N11 | SD | Linear N12 | SD |
| | 22.52 | 0.05 | 20.81 | 0.08 | 20.65 | 0.07 | 21.23 | 0.12 |
| | 23.50 | 0.04 | 23.37 | 0.07 | 23.59 | 0.02 | 22.89 | 0.13 |
| | 23.31 | 0.25 | 22.95 | 0.07 | 23.22 | 0.03 | 22.24 | 0.28 |
| | 23.10 | 0.33 | 22.71 | 0.17 | 22.91 | 0.24 | 22.74 | 0.28 |
| | 28.39 | 0.29 | 28.83 | 0.15 | 31.90 | 0.23 | 31.15 | 0.38 |
| | 21.07 | 0.04 | 18.90 | 0.10 | 18.88 | 0.16 | 19.12 | 0.05 |

TABLE 6.1-continued

| Linear N9 | SD | Linear N10 | SD | Linear N11 | SD | Linear N12 | SD |
|---|---|---|---|---|---|---|---|
| 40.00 | 0.00 | 40.00 | 0.00 | 40.00 | 0.00 | 40.00 | 0.00 |
| 40.00 | 0.00 | 40.00 | 0.00 | 40.00 | 0.00 | 40.00 | 0.00 |
| 40.00 | 0.00 | 40.00 | 0.00 | 40.00 | 0.00 | 40.00 | 0.00 |
| 40.00 | 0.00 | 40.00 | 0.00 | 40.00 | 0.00 | 40.00 | 0.00 |
| 39.22 | 1.10 | 40.00 | 0.00 | 40.00 | 0.00 | 40.00 | 0.00 |
| 35.17 | 0.04 | 36.13 | 0.39 | 35.27 | 0.42 | 35.00 | 0.52 |

| Loop N9 | SD | Loop N10 | SD | Loop N11 | SD | Loop N12 | SD |
|---|---|---|---|---|---|---|---|
| 22.32 | 0.03 | 22.08 | 0.30 | 21.65 | 0.41 | 21.54 | 0.08 |
| 22.99 | 0.01 | 23.98 | 0.06 | 24.08 | 0.19 | 23.79 | 0.35 |
| 24.09 | 0.17 | 23.83 | 0.07 | 23.03 | 0.16 | 24.08 | 0.01 |
| 27.46 | 0.47 | 28.00 | 0.26 | 24.28 | 0.03 | 25.10 | 0.28 |
| 38.80 | 1.69 | 40.00 | 0.00 | 40.00 | 0.00 | 40.00 | 0.00 |
| 21.77 | 0.24 | 23.22 | 0.07 | 23.23 | 0.05 | 22.07 | 0.27 |

| Loop N9 | Loop N9 | Loop N10 | Loop N10 | Loop N11 | Loop N11 | Loop N12 | Loop N12 |
|---|---|---|---|---|---|---|---|
| 40.00 | 0.00 | 40.00 | 0.00 | 40.00 | 0.00 | 40.00 | 0.00 |
| 40.00 | 0.00 | 40.00 | 0.00 | 40.00 | 0.00 | 40.00 | 0.00 |
| 40.00 | 0.00 | 40.00 | 0.00 | 40.00 | 0.00 | 40.00 | 0.00 |
| 40.00 | 0.00 | 40.00 | 0.00 | 40.00 | 0.00 | 40.00 | 0.00 |
| 40.00 | 0.00 | 40.00 | 0.00 | 40.00 | 0.00 | 40.00 | 0.00 |
| 40.00 | 0.00 | 38.67 | 0.47 | 36.78 | 1.73 | 40.00 | 0.00 |

As will be appreciated by one of skill in the art, such a length for a random sequence would be unacceptable for supported oligo ligation detection sequencing because of the possibility of altering the target sequence by mismatches in the priming hybrid. Thus, in some embodiments, it is especially advantageous to use the above linear primer when techniques similar to (and including) supported oligo ligation detection sequencing are to be used.

EXAMPLE 7

Comparison of Amplification Ability of Linear and Looped Primers

Figure 13A:
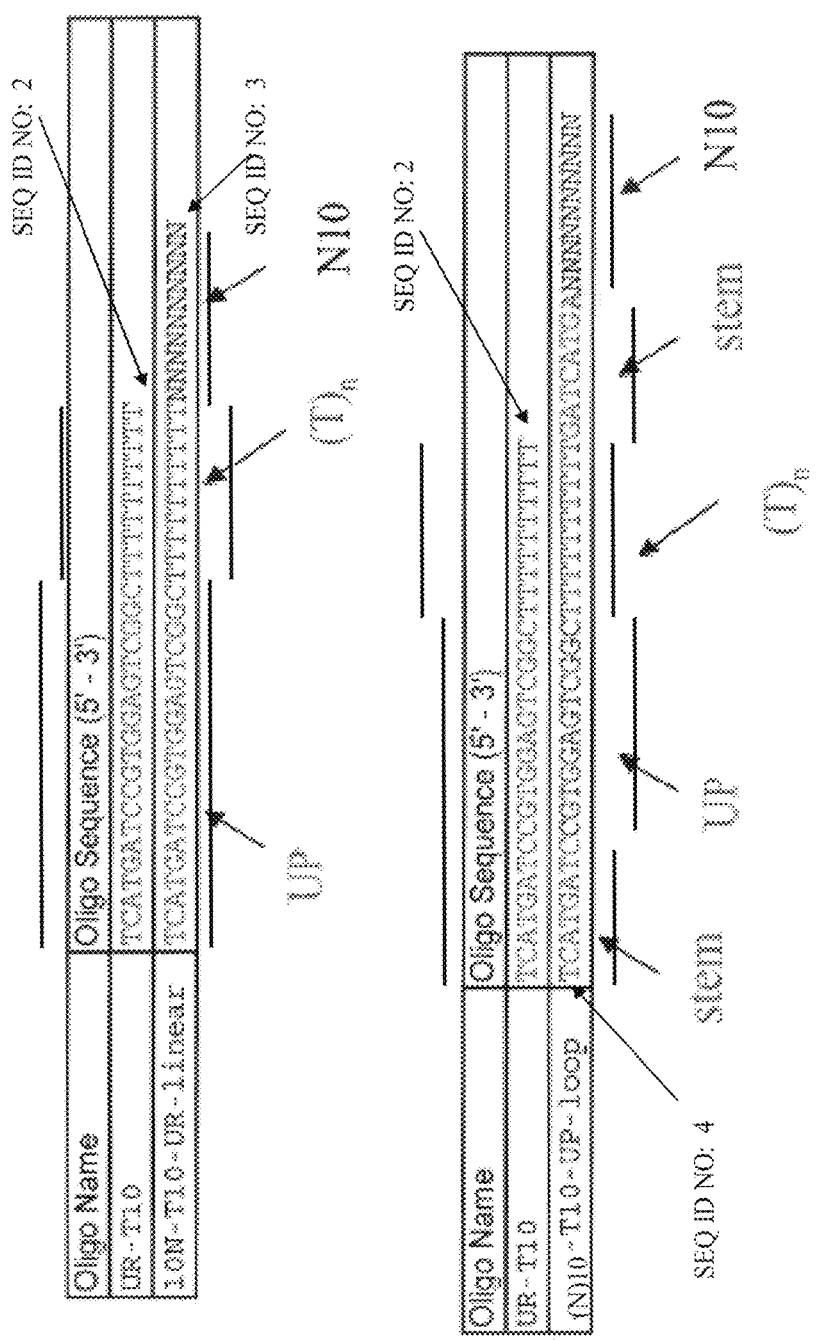
FIG. 13A depicts an example of a linear primer and a loopable primer.

The present example demonstrates the ability of linear and looped primers to amplify various initial amounts of a target sample DNA. The various primers that were used are depicted in FIG. 13A. The top primer, 10N-T10-UR, is the linear primer and the second primer, (N)10-T10-UP, is the looped primer.

The protocol for the experiment is depicted in Table 7.1 below. This protocol was also used for the results in FIGS. 12A and 12B.

TABLE 7.1

| Whole genome Amplification | stock concen-tratoins (uM) | Final cocen-tration (uM) | Final cocen-tration |
|---|---|---|---|
| step 1 extension and pre-PCR | | | |
| 10xPCR buffer II | 2 | 10 | 1 |
| DNA-template | 4 | 0 | 0 |
| N8-UR-T10 (100 uM) | 2 | 100 | 10 | (10 uM) |
| AmpliTaq 5 u/ul | 4 | 5 | 1 | (1 Unit/ul) |
| dNTP 100 mM | 1 | 100 | 5 | (5 mM) |
| MgCl2 25 mM | 2.4 | 25 | 3 | (3.0 mM) |
| H2O | 4.5 | | |
| total volume | 20 | | |
| dilution factor | 5 | | |

TABLE 7.1-continued

| Whole genome Amplification | stock concen-tratoins (uM) | Final cocen-tration (uM) | Final cocen-tration |
|---|---|---|---|
| 95 C. 1 min (95 C. 15 sec -16 C. 2 min-35 C. 2 min-65 C. 2 min) 20 cycles step 2 further extension and pre-PCR | | | |
| 10xPCR buffer II | 4 | 10 | 1 |
| above reagent | 20 | | 0 |
| UR-T10 100 uM | 4 | 100 | 10 | (10 uM) |
| dNTP 100 mM | 1 | 100 | 2.5 | (2.5 mM) |
| MgCl2 25 mM | 2.4 | 25 | 1.5 | (1.5 mM) |
| AmpliTaq 5 u/ul | 4 | 5 | 0.5 | (0.5 u/ul) |
| H2O | 4.6 | | 0 |
| total volume | 40 | | |
| dilution factor | 10 | | |
| 95 C. 1 min (95 C. 15 sec -65 C. 2 min-72 C. 2 min) 25x step 3 PCR clean up | | | |
| 10 ul above product + 4 ul ExoSAP 37 C. 15 min, 85 C. 5 min above 14 ul product + dH2O 186 ul = 200 ul for 48 gene | | | |
| dilution factor | 200 | | |

Figure 13B:
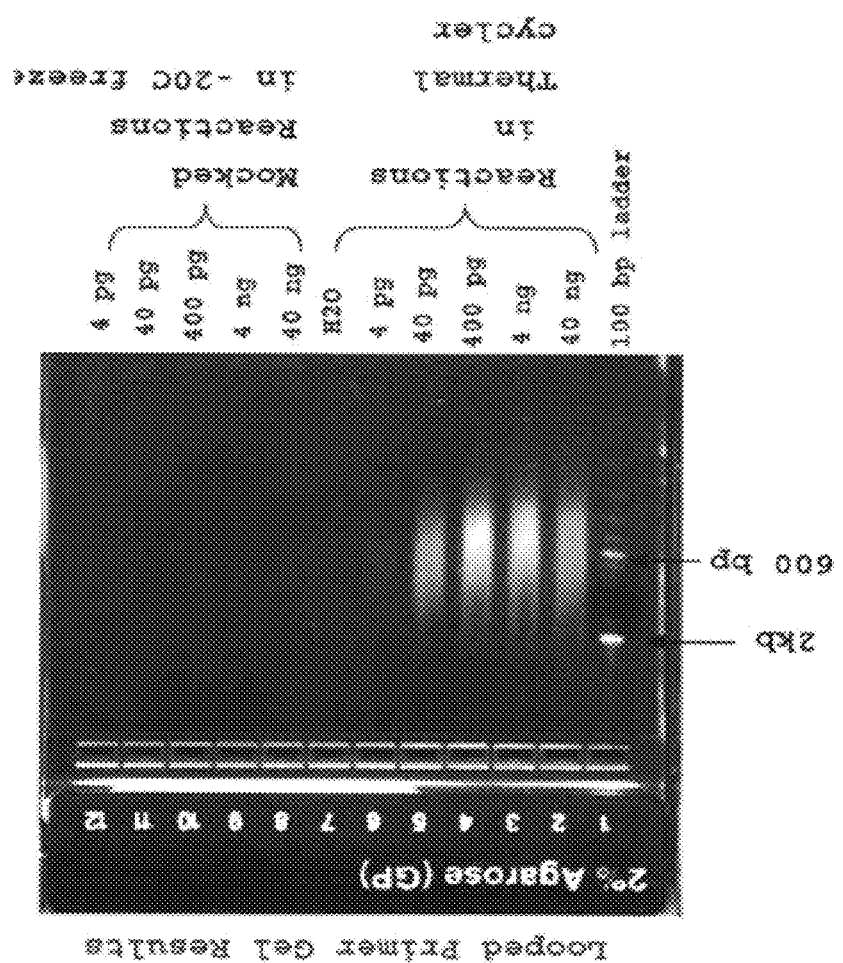
FIG. 13B is a representation of a gel demonstrating the results of amplification from various concentrations of starting material using a looped primer.
Figure 13C:
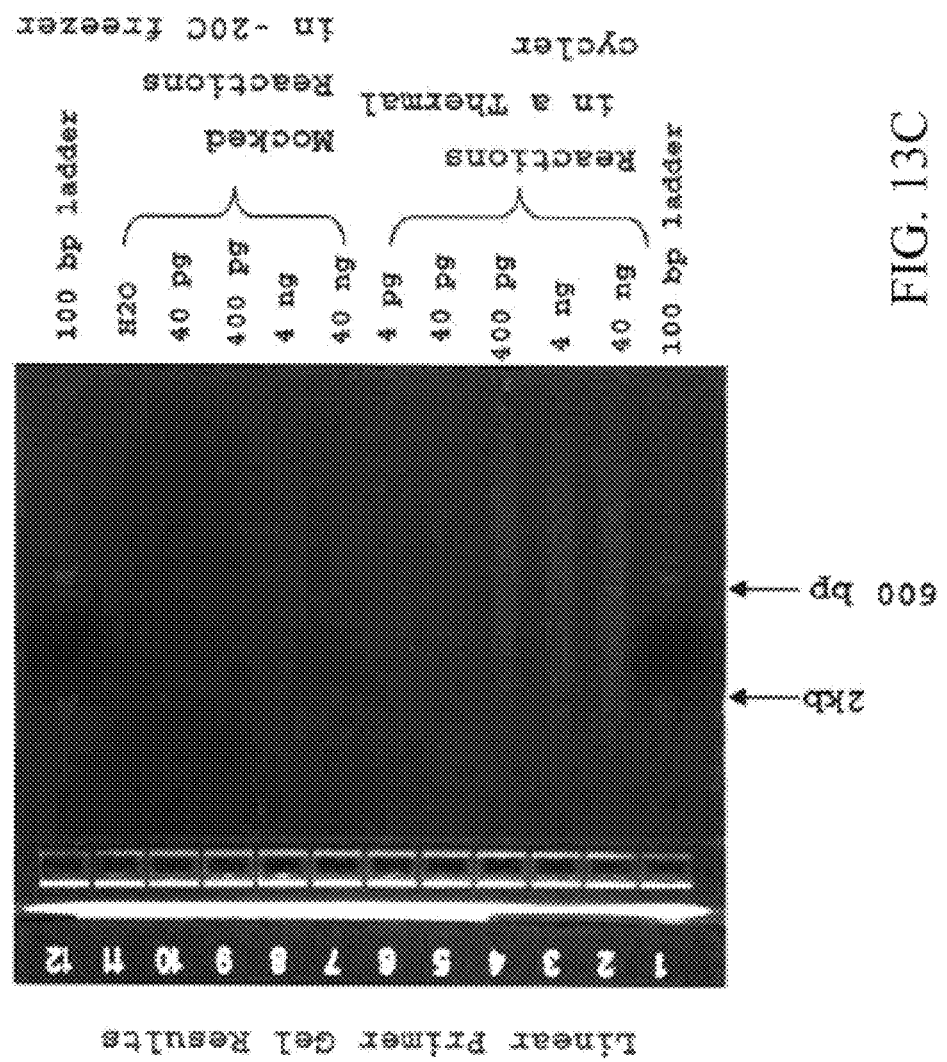
FIG. 13C is a representation of a gel demonstrating the results from various concentrations of starting material using a linear primer.

Varying amounts of starting target (CEPH gDNA) were used, from 0 to 40 ng for both the linear and the looped primer to compare the ability of the two primer types in amplifying the desired target type. The results for the looped primer are depicted in Table 7.2 and FIG. 13B. The results for the linear primer are depicted in Table 7.3 and FIG. 13C. It is noted that the staining conditions between 13B and 13C are different; thus, the figures should not be interpreted to indicate that one form of primer worked better than another.

TABLE 7.2

| | Rnase P Looped primers | | | | |
|---|---|---|---|---|---|
| CEPH gDNA | real Cts | SD | Mocked Cts | SD | Amplification Folds | SD |
| 40 ng | 22.68 | 0.01 | 33.98 | 0.66 | 2661 | 1174 |
| 4 ng | 23.01 | 0.15 | 37.05 | 1.08 | 18736 | 11385 |
| 400 pg | 23.86 | 0.13 | 39.46 | 0.77 | 1700 | 997 |
| 40 pg | 38.04 | 2.77 | 38.93 | 1.51 | 2 | 2 |
| 4 pg | 39.17 | 1.17 | 40.00 | 0.00 | 2 | 2 |
| 0 pg | 40.00 | 0.00 | 40.00 | 0.00 | 1 | 0 |

TABLE 7.3

| | Rnase P Lineat N10-primers | | | | |
|---|---|---|---|---|---|
| CEPH gDNA | real Cts | SD | Mocked Cts | SD | Amplification Folds | SD |
| 40 ng | 18.45 | 0.16 | 33.98 | 0.66 | 48653 | 16524 |
| 4 ng | 18.71 | 0.14 | 37.05 | 1.08 | 393312 | 298253 |
| 400 pg | 20.49 | 0.34 | 39.46 | 0.77 | 590200 | 414125 |
| 40 pg | 24.88 | 0.04 | 38.93 | 1.51 | 22046 | 20005 |
| 4 pg | 40.00 | 0.00 | 40.00 | 0.00 | 1 | 0 |
| 0 pg | 40 | 0 | 40 | 0 | 1 | 0 |

As can be seen in the results, the products of the looped primers were, comparatively, in the same size range, while the linear primers resulted in a larger diversity of sizes. In addition, as shown in the above tables, the cycle thresholds from the TaqMan results demonstrated that the linear primer generally had a lower cycle threshold than the looped primers.

As will be appreciated by one of skill in the art, a variety of parameters for the above example can be altered. For example, in some embodiments, $(T)_n$ is between 0 and 10 nucleotides (so there is no noncomplementary region). In addition, $(N)_{10}$ can include a population of 3' target specific regions of various lengths (for example, $(N)_n$, n=5-12). These parameters can apply to the above example, as well as any of the other embodiments described herein.

EXAMPLE 8

Impact of Varying the Number of PCR Cycles in Step 2

The impact of varying the number of PCR cycles in step number 2 (FIG. 8) was examined for the looped N8-T10-UR and UP primers. As shown in Table 8.1, 14 cycles of PCR (using looped N10-T10-UR primer) resulted in a better dose response, but it required 400 pg of gDNA input for the results.

TABLE 8.1

| | Rnase P Assay | | | |
|---|---|---|---|---|
| CEPH gDNA | N10-T10-UP step2 × 14 (Ct) | N10-T10-UP SD | N10-T10-UP step2 × 20 (Ct) | N10-T10-UP SD |
| 40 ng | 26.98 | 0.22 | 22.41 | 0.11 |
| 4 ng | 27.98 | 0.32 | 23.00 | 0.13 |
| 400 pg | 29.47 | 0.22 | 24.94 | 0.11 |
| 40 pg | 35.59 | 0.01 | 29.26 | 0.03 |
| 4 pg | 37.12 | 0.82 | 36.13 | 0.73 |
| NTC | 38.81 | 1.68 | 39.62 | 0.53 |

Figure 14:
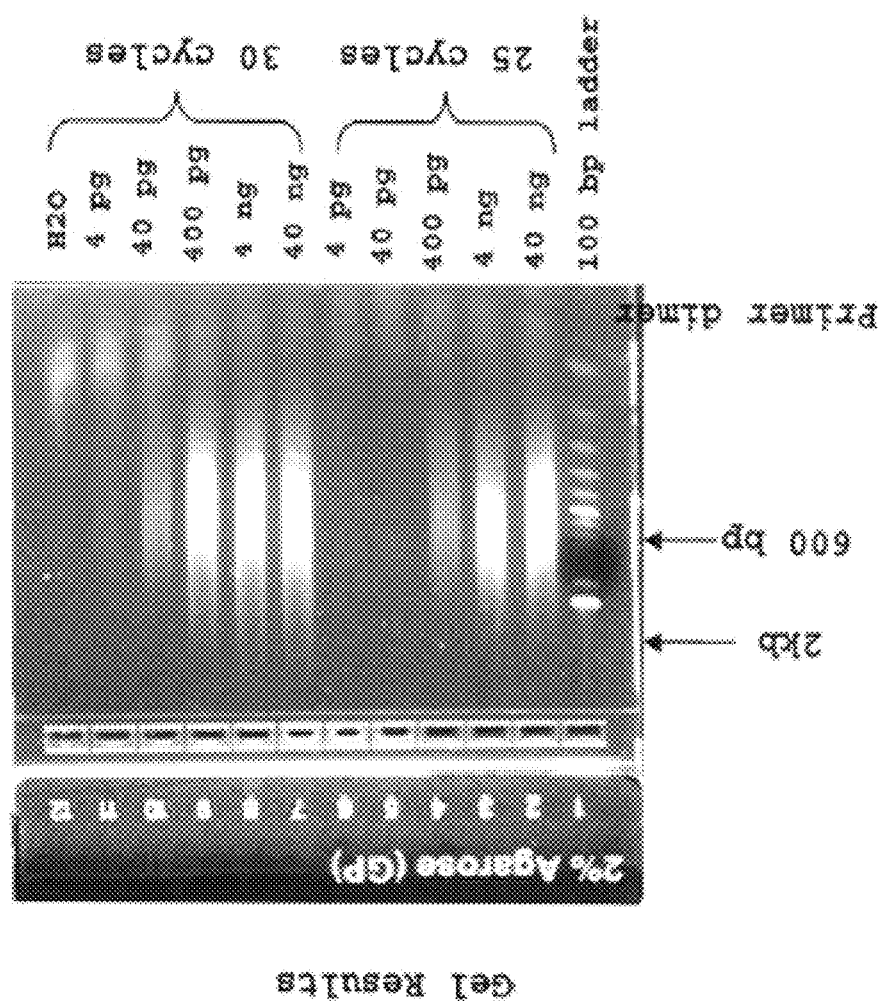
FIG. 14 is a representation of a gel demonstrating the results of amplification from various concentrations of starting material using 25 or 30 cycles.

Interestingly, 30 cycles of PCR (using looped N10-T10-UR) resulted in saturated output (see Table 8.2 and FIG. 14); however, for single cell inputs (e.g., 3 pg), 30 cycles would be an appropriate amount.

TABLE 8.2

| | Rnase P Assay | | | |
|---|---|---|---|---|
| CEPH gDNA | N10-T10-UP step2 × 25 (Ct) | N10-T10-UP SD | N10-T10-UP step2 × 30 (Ct) | N10-T10-UP SD |
| 40 ng | 18.61 | 0.06 | 15.72 | 0.37 |
| 4 ng | 18.65 | 0.36 | 15.63 | 0.08 |
| 400 pg | 20.10 | 0.06 | 15.15 | 0.22 |
| 40 pg | 34.24 | 0.45 | 17.84 | 0.11 |
| 4 pg | 34.01 | 0.30 | 34.58 | 0.38 |
| NTC | 34.15 | 0.20 | 33.92 | 0.36 |

EXAMPLE 9

Primer Pools

As will be appreciated by one of skill in the art, in many of the embodiments described above, loop amplification can be achieved based on knowing which sequence was (or should be) contained within the loop, such as RNase P. In situations in which the target within the loop is not initially known, such as when an entire genome is being amplified, the protocol can be varied slightly to take this variable into account. For example, indiscriminant primers could be used. Alternatively, and as described in this example, numerous primers can be tested or used on the amplified sample.

Following any of the above initial amplification procedures (e.g., at a point following the formation of the double-extended linear primer, but prior to the use of a insert amplification primer) one can divide the amplified product into numerous subsamples. Each subsample will simply be a fraction of the amplified product, and thus can include a representative (e.g., proportionate and substantially complete) distribution of the various double-extended linear primers. Each subsample can be placed in a separate well, to which a specific known, or knowable, insert amplification primer, or primers, can be added. Following this, an amplification step can be performed in each of the wells. This will allow for the amplification of the insert section. These amplified sequences can then be detected, such as by sequencing.

EXAMPLE 10

STR Amplification

The present example demonstrates how one can use the methods and primers described herein to amplify a STR locus of interest.

At least one linear primer, having a 3' target specific region that will bind near a locus to be examined, is combined with a sample that includes a target nucleic acid sequence. The 3' target specific region can be selected so that it binds near at least one of the following loci: TH01, TPOX, CSF1PO, vWA, FGA, D3S1358, D5S818, D7S820, D13S317, D16S539, D8S1179, D18S51, D21S11, D2S1338, D3S1539, D4S2368, D9S930, D10S1239, D14S118, D14S548, D14S562, D16S490, D16S753, D17S1298, D17S1299, D19S253, D19S433, D20S481, D22S683, HUMCSF1PO, HUMTPOX, HUMTH01, HUMF13AO1, HUMBFXIII, HUMLIPOL, HUMvWFA31, Amelogenin, D12s391, D6S1043, SE33, or any combination thereof. The amplification outlined in any of the above examples or embodiments can be performed, thereby resulting in the amplification of the relevant locus.

EXAMPLE 11

STR Amplification

The present example demonstrates how one can use the methods and primers described herein to amplify a STR locus of interest.

At least one linear primer having a 3' target specific region that comprises a degenerate region, is combined with a sample that includes a target nucleic acid sequence. The linear primer is used to amplify the target nucleic acid sequence as provided in any of the above examples. However, once the double extended linear primer is created, the insert amplification primers that are used are selected so that the insert amplification primers bind near at least one of the following loci: TH01, TPOX, CSF1PO, vWA, FGA, D3S1358, D5S818, D7S820, D13S317, D16S539, D8S1179, D18S51, D21S11, D2S1338, D3S1539, D4S2368, D9S930, D10S1239, D14S118, D14S548, D14S562, D16S490, D16S753, D17S1298, D17S1299, D19S253, D19S433, D20S481, D22S683, HUMCSF1PO, HUMTPOX, HUMTH01, HUMF13AO1, HUMBFXIII, HUMLIPOL, HUMvWFA31, Amelogenin, D12s391, D6S1043, and SE33. This will then allow for the amplification of the STR at the relevant locus.

As will be appreciated by one of skill in the art, numerous insert amplification primers can be used for the above processing, e.g., 2-10, 10-50, 50-100, 100-1000, 1000-10,000, 10,000-30,000, 30,000-40,000, 40,000-50,000, 50,000-100,000, or more primers. Each can be used in a separate well with a representative portion of the amplified target nucleic acid sequence. As will be appreciated by one of skill in the art, during the amplification, the conditions should be such that the double-extended linear primer is self-hybridized, resulting in the selective amplification of the initially amplified products of the desired size.

The present disclosure clearly establishes that the presently disclosed processes can be effective in selectively amplifying usefully sized fragments throughout relatively long stretches of gDNA from a target sample. While the above embodiments have been described in terms of a linear primer, in other embodiments, the initial primer can be looped or need not be linear (as long as there is a universal region that is placed on one end and its complement is placed on the other end of a section of nucleic acid to be amplified. Thus, in some embodiments, any or every one of the above embodiments can be used with a stem-looped primer instead of a linear primer.

Furthermore, in some embodiments, the amount of amplification is, compared to the current state of the art, very high (approximately 3000 fold to over hundreds of thousands fold), while still amplifying the larger fragments. This is in contrast to previous attempts at amplification using random primers that appeared to generally reach lower levels of amplification. (See, e.g., Zhang et al., PNAS, vol. 89, 5847-5851, (1992), approximately 30 fold; and Genomeplex® Whole Genome Amplification (WGA) Kit by Sigma-Aldrich, discussed on the world wide web at biocompare.com/review/769/Genomeplex-Whole-Genome-Amplification-(WGA)-Kit-by-Sigma-Aldrich.html, discussing 3000 fold). Additionally, as shown above, the amplification ability can be enhanced through the use of an Exo I digestion step, although this is clearly not required. It is believed that these data demonstrate that 3' target-specific portions (e.g., degenerate regions) of 7-15 nucleic acids in length will work for some embodiments. Additionally, in some embodiments these relatively large increases in amplification are achieved while still maintaining some degree of dose response during the amplification. For example, in some embodiments, relatively small amounts of one species to be amplified will still be a relatively small percent of the amplified product (although it could have been amplified, e.g., 100-1,000,000 times).

In this disclosure, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. The phrase "and/or" denotes a shorthand way of indicating that the specific combination is contemplated in combination and, separately, in the alternative.

The section headings used herein are for organizational purposes only and are not to be construed as limiting the described subject matter in any way.

It will be appreciated that there is an implied "about" prior to the temperatures, concentrations, times, etc. discussed in the present teachings, such that slight and insubstantial deviations are within the scope of the present teachings herein. For example, "a primer" means that more than one primer can, but need not, be present; for example but without limitation, one or more copies of a particular primer species, as well as one or more versions of a particular primer type, for example but not limited to, a multiplicity of different linear primers. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method of amplifying a nucleic acid sequence, comprising:
   a) generating a plurality of cDNA target sequences by a performing reverse transcription reaction on a plurality of RNA;
   b) hybridizing the plurality of cDNA target sequences with a plurality of first linear primers which contain (i) a terminal 3' region having a first unconstrained random sequence and (ii) a 5' region having a first universal sequence,
      wherein the first unconstrained random sequences of the terminal 3' region include inosine, adenosine, guanosine, and cytidine, and the first random sequences exclude thymidine,
      wherein the plurality of the first linear primers include different random sequences,
      wherein the random sequences hybridize to a sequence of the plurality of cDNA target sequences, and
      wherein the plurality of the first linear primers include the same universal sequence which does not hybridize to the plurality of cDNA target sequences; and
   c) forming a plurality of extended linear primer products by extending the first linear primers that are hybridized to the plurality of cDNA target sequences;

d) hybridizing the plurality of the extended linear primer products to a plurality of second linear primers which contain (i) a terminal 3' region having a second unconstrained random sequence and (ii) a 5' region having a second universal sequence,
  wherein the second random unconstrained sequences of the terminal 3' region include inosine, adenosine, guanosine, and cytidine, and the second random sequences exclude thymidine,
  wherein the plurality of the second linear primers include different random sequences, and
  wherein the random sequences hybridize to a portion of the extended linear primer products,
  wherein the plurality of the second linear primers include the same universal sequence as the universal sequence in the first linear primers; and
e) forming a plurality of double-extended linear primer products by extending the plurality of second linear primers that are hybridized to the plurality of the extended linear primer products.

2. The method of claim 1, further comprising: forming a plurality of hairpin structures by intramolecular hybridizing the plurality of double-extended linear primer products in step (e).

3. The method of claim 1, further comprising: sequencing the double-extended linear primer products in step (e).

4. The method of claim 1, further comprising: forming amplification products by amplifying the plurality of double-extended linear primer products of step (e) in a single primer amplification reaction with a plurality of amplification primers that hybridize to the first or the second universal sequence regions of the plurality of double-extended linear primer products.

5. The method of claim 4, further comprising: forming a plurality of hairpin structures by intramolecular hybridizing the amplification products.

6. The method of claim 4, further comprising: sequencing the amplification products.

7. The method of claim 1, further comprising: forming amplification products by amplifying the plurality of double-extended linear primer products of step (e) in an exponential amplification reaction with (i) a plurality of amplification primers that hybridize to the first universal sequence regions of the plurality of double-extended linear primer products, and (ii) a plurality of amplification primers that hybridize to the second universal sequence regions of the plurality of double-extended linear primer products.

8. The method of claim 7, further comprising: forming a plurality of hairpin structures by intramolecular hybridizing the amplification products.

9. The method of claim 7, further comprising: sequencing the amplification products.

10. The method of claim 1, wherein the first and second random sequences in the terminal 3' regions of the first and second linear primers is 4-12 nucleotides in length.

11. The method of claim 1, wherein the plurality of RNA is isolated from a single cell.

12. The method of claim 1, wherein the plurality of RNA is isolated from fewer than 10 cells.

13. The method of claim 1, wherein the plurality of RNA is isolated from fewer than 100 cells.

14. The method of claim 1, wherein the plurality of RNA is isolated from a tumor.

* * * * *